US011105950B2

(12) United States Patent  
Allen

(10) Patent No.: US 11,105,950 B2  
(45) Date of Patent: Aug. 31, 2021

(54) WHOLE-BODY TRANSMISSION X-RAY SCANNER AND METHODS FOR WHOLE-BODY SCANNING

(71) Applicant: John R. Allen, Port Jefferson Station, NY (US)

(72) Inventor: John R. Allen, Port Jefferson Station, NY (US)

( * ) Notice: Subject to any disclaimer, the term of this patent is extended or adjusted under 35 U.S.C. 154(b) by 16 days.

(21) Appl. No.: 16/690,692

(22) Filed: Nov. 21, 2019

(65) Prior Publication Data

US 2020/0088905 A1 Mar. 19, 2020

Related U.S. Application Data

(63) Continuation-in-part of application No. PCT/US2018/051300, filed on Sep. 17, 2018, which  
(Continued)

(51) Int. Cl.  
*G01N 23/00* (2006.01)  
*G01V 5/00* (2006.01)  
(Continued)

(52) U.S. Cl.  
CPC ......... *G01V 5/0016* (2013.01); *G01N 24/084* (2013.01); *A61B 6/4441* (2013.01)

(58) Field of Classification Search  
CPC .................................................. A61B 6/4435  
See application file for complete search history.

(56) References Cited

U.S. PATENT DOCUMENTS 2,281,931 A  5/1942  Frank  
3,101,407 A  8/1963  Shipman, Jr.  
(Continued)

FOREIGN PATENT DOCUMENTS

EP    0807403 A2    11/1997  
WO    2016028617 A1    2/2016

OTHER PUBLICATIONS

International Search Report & Written Opinion for PCT/US2018/051300 dated Nov. 21, 2018.

*Primary Examiner* — Dani Fox  
(74) *Attorney, Agent, or Firm* — Gregory L. Mayback; Dickinson Wright PLLC

(57) ABSTRACT

A whole-body transmission x-ray scanner includes a collimated x-ray source, a linear x-ray camera configured to detect x-rays, a counterweight, and a positioner that aligns the source and ray camera and moves the source and camera synchronously to scan and acquire radiographic images of an object located therebetween. The positioner comprises a cable alignment assembly connecting the counterweight directly to the x-ray source and camera to maintain alignment of the source and camera during a scanning mode in which the source and camera move from one end of the object to another end. The positioner comprises a motor, a bi-directional crossover slide track bearing assembly connected to the source, and a conveyor operatively connected to the motor and to the slide track bearing assembly to move the slide track bearing assembly in a loop that correspondingly translates the source and camera along a single linear axis.

20 Claims, 12 Drawing Sheets

Related U.S. Application Data is a continuation of application No. 16/042,219, filed on Jul. 23, 2018, now Pat. No. 10,520,636.

(60) Provisional application No. 62/615,746, filed on Jan. 10, 2018, provisional application No. 62/572,065, filed on Oct. 13, 2017.

(51) Int. Cl.
  *G01N 24/08* (2006.01)
  *A61B 6/00* (2006.01)

(56) References Cited

U.S. PATENT DOCUMENTS

| | | |
|---|---|---|
| 6,611,364 B1 | 8/2003 | Craig et al. |
| 6,851,851 B2 | 2/2005 | Smith et al. |
| 6,940,948 B1 | 9/2005 | Tretiakov et al. |
| 7,540,660 B2 | 6/2009 | Koyanagi |
| 7,561,666 B2 | 7/2009 | Annis |
| 7,809,109 B2 | 10/2010 | Mastronardi et al. |
| 7,854,551 B2 | 12/2010 | Lv et al. |
| 8,073,100 B2 | 12/2011 | Pohjoispuro et al. |
| 8,477,902 B2 | 7/2013 | Li et al. |
| 8,934,603 B2 | 1/2015 | Magnuson et al. |
| 2009/0060129 A1 | 3/2009 | Kang et al. |
| 2010/0232574 A1 | 9/2010 | Ahn |
| 2012/0177176 A1 | 7/2012 | Carver et al. |
| 2016/0331335 A1 | 11/2016 | Gregerson et al. |
| 2017/0038484 A1* | 2/2017 | Cox .................. G01T 1/243 |

* cited by examiner

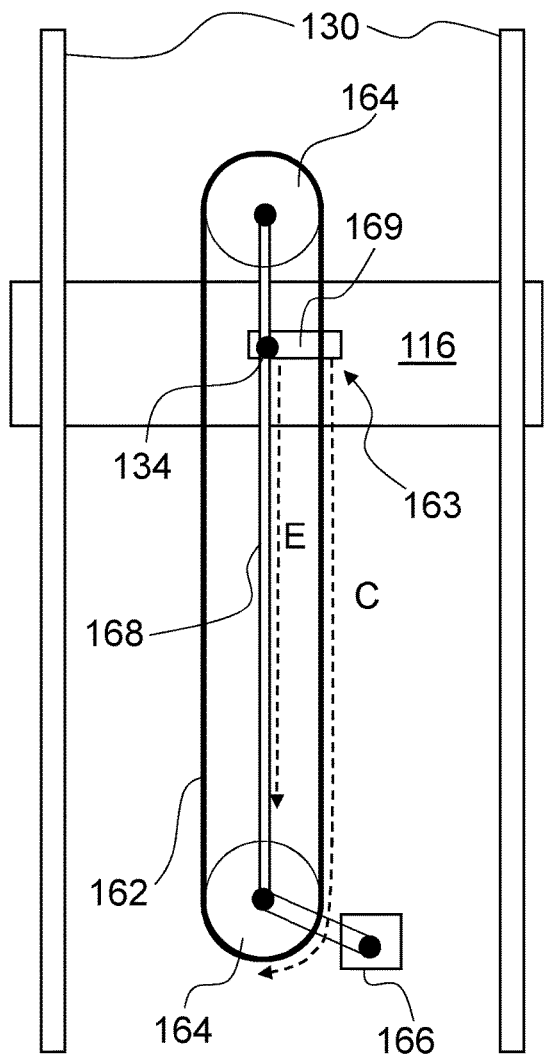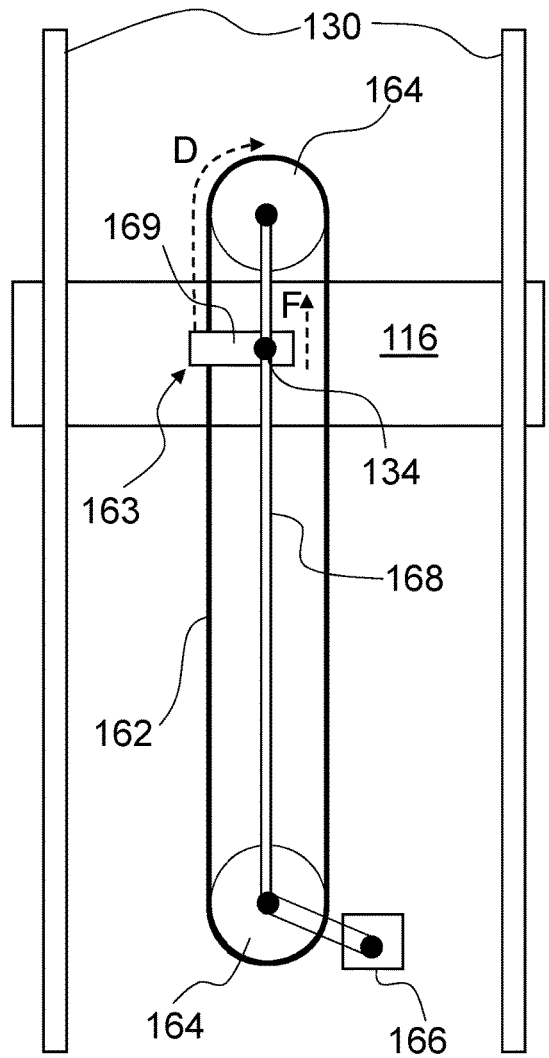
FIG. 15  FIG. 16

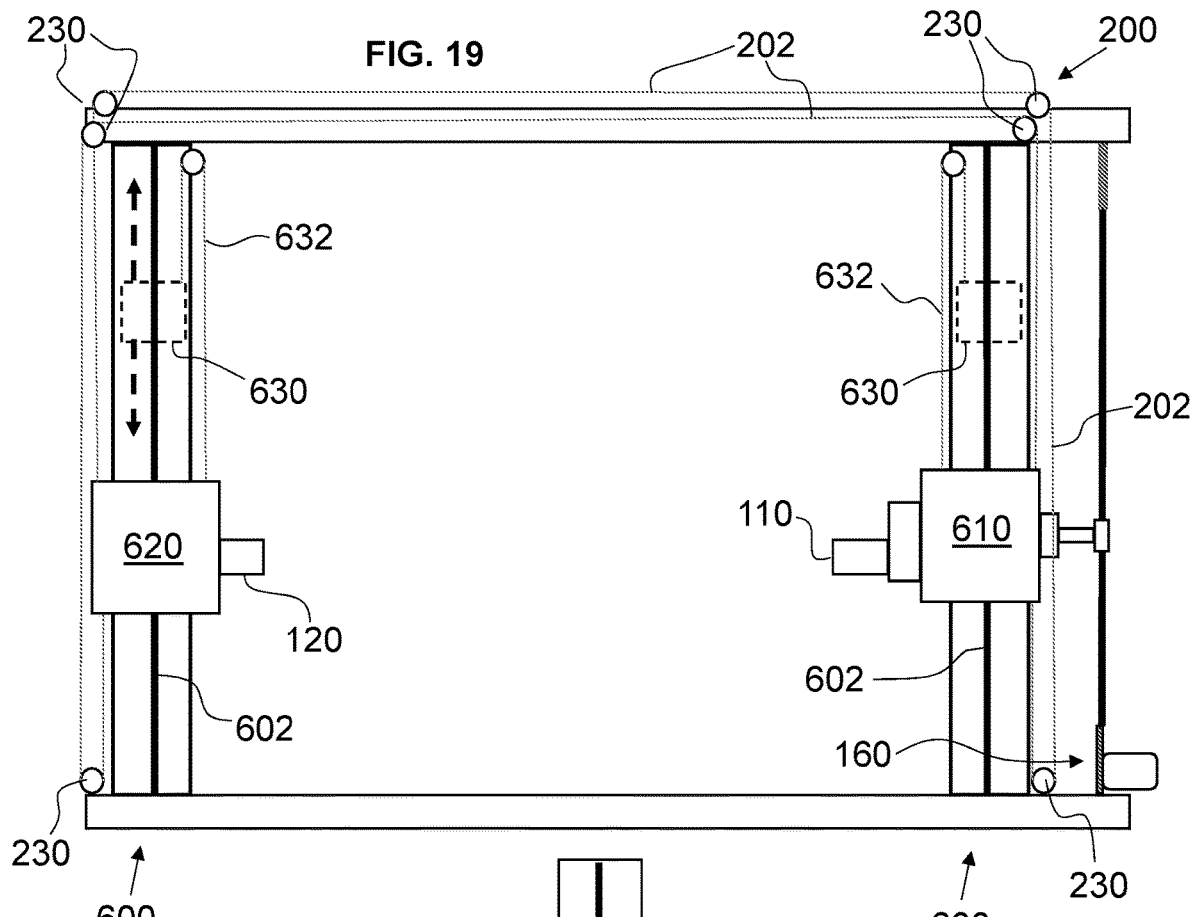
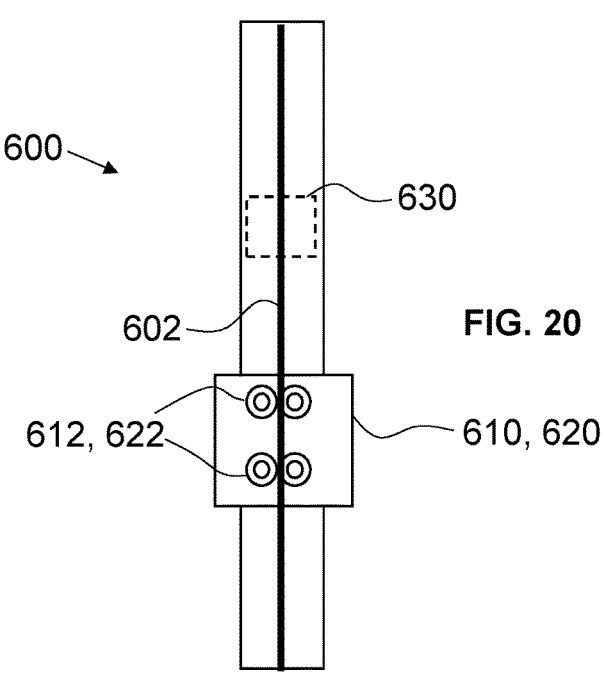

WHOLE-BODY TRANSMISSION X-RAY SCANNER AND METHODS FOR WHOLE-BODY SCANNING

CROSS-REFERENCE TO RELATED APPLICATIONS

This application is a continuation-in-part application, under 35 U.S.C. § 120, of copending international application No. PCT/US2018/051300, filed Sep. 17, 2018, which designated the United States and claims the priority, under 35 U.S.C. § 119, of U.S. patent application Ser. No. 16/042,219, filed Jul. 23, 2018, which application claims priority, under 35 U.S.C. § 119, of U.S. Provisional Patent Application Nos. 62/615,746, filed Jan. 10, 2018, and 62/572,065, filed Oct. 13, 2017; the prior applications are herewith incorporated by reference in their entirety.

STATEMENT REGARDING FEDERALLY SPONSORED RESEARCH OR DEVELOPMENT

Not Applicable

FIELD OF THE INVENTION

The present systems, apparatuses, and methods lie in the field of x-ray scanning. The present disclosure relates generally to an x-ray scanner and methods of x-ray scanning that produce radiographic images of the whole human body. The scanner produces whole-body transmission radiographic images of a person in a standing or prone position while the person remains stationary. Applications for whole-body radiographic imaging include contraband detection and medical diagnosis, for example. Other applications include imaging objects such as cargo and personal effects for security reasons. The systems, apparatuses, and methods incorporate a collimated x-ray source, a linear x-ray camera, a user interface, and a positioner that moves the x-ray source and x-ray camera in a synchronous motion to scan and acquire radiographic images. An exemplary embodiment of a positioner incorporates a single-motor-conveyor-belt-drive with a bi-directional crossover bearing assembly, a closed-looped-cable-alignment system, an operator control station, and a selectable manual or continuous x-ray scanning. In a manual mode, the scan mode passes through one cycle and stops until a next scan is executed. In a continuous mode, the scan mode runs in a continuous loop and x-rays will be generated when the x-ray tube and camera are in a downward motion. The x-ray stops when the x-ray tube and camera reach the bottom and, then, the system continues to move, allowing the person who was just scanned to move out of the scanning area and the next person to enter and step into position so that, when the system is ready for the next x-ray scan, the next person is in position for scanning.

BACKGROUND OF THE INVENTION

Transmission x-ray scanner designs for whole-body radiographic imaging have been described in the patent literature for over fifty years. One such system is described in U.S. Pat. No. 3,101,407 to Shipman, which issued on Aug. 20, 1963. In Shipman, the source and the camera are moved directly with cables and pulleys connected to a motor. Scanning starts from a parked stop, accelerates to a scanning speed, and then decelerates to a parked stop. This change in motion is repeated for the next scan. This movement introduces error into the detected image and produces motion artifacts in the image. The scanner taught by Shipman suffers from several limitations. One of the primary limitations is the complexity of the positioner (drive and cable mechanisms) used to move the x-ray source and linear x-ray camera and support the person being scanned. Such a drive-and-cable system is too complex to be practical or cost effective. The system also was designed to move slowly. Another limitation is that the motion of the x-ray source and linear x-ray camera can only move in one direction at a time, either up or down. Once the source/camera arrives at a limit of travel in either direction, it must come to a full stop and reverse direction. This creates a need to accelerate the x-ray source and linear x-ray camera when starting and stopping the scan, which also introduces the problem of gear backlash that must be compensated for when reversing the motor direction.

Another prior art system is described in U.S. Pat. No. 8,477,902 to Li et al., issued on Jul. 2, 2013. This patent describes a system having two independent vertical towers: one tower for the x-ray source and a second tower for a linear x-ray camera. The x-ray source and the linear x-ray camera are each driven by separate motors and are kept in alignment by a phasemeter. This technology has limitations with respect to vertical travel and maintaining alignment. More specifically, the motors require a start and stop distance that has effect on the scanning travel distance that can be accomplished at a constant speed. In this design, motor backlash is an issue and must be addressed and compensated for when reversing direction.

SUMMARY OF THE INVENTION

The systems, apparatuses, and methods described provide a whole-body transmission x-ray scanner that overcomes the hereinafore-mentioned disadvantages of the heretofore-known devices and methods of this general type and that provide such features with a novel design that greatly simplifies the structure for synchronously scanning the x-ray source and the linear x-ray camera to image a stationary person using a positioner comprising a single motor-conveyor-loop chain/belt-drive, a novel bi-directional crossover bearing slide track, and a closed loop cable alignment system.

The positioner employs a vertical conveyor drive system connected to the x-ray source by a novel bi-directional crossover slide bearing mechanism. Use of the bi-directional crossover slide bearing mechanism permits the x-ray source to move up and down without having to compensate for the start or stop motor acceleration and lag and without changing the direction of the drive motor from up to down motion and, therefore, eliminates all need for motor-drive backlash compensation. At the start of a scan, the distance traveled during acceleration of the motor drive is best compensated for when the scan direction is downward so that there is room to allow the motor to come up to a constant velocity before exposing the person. A closed-loop cable system connecting the x-ray source to the linear x-ray camera remains in constant tension and, therefore, moves the linear x-ray camera in a synchronous motion to stay in alignment with the x-ray source. The closed-loop cable alignment system also keeps the x-ray source assembly and the x-ray camera assembly stable by damping vibration while moving limiting motion artifacts as well as venetian blind effect. Counterweights are used to balance the load so that, when the x-ray source and x-ray camera move up and down together, they present the same resistance to the drive motor in either direction, thereby placing less load-stress on the motor drive assemblies.

In an exemplary embodiment, both the x-ray source and the x-ray camera are connected directly to the counterweight. The vertical scanning x-ray system comprises a bi-directional crossover slide-track assembly, a positioner comprising a closed-loop, vertical indexing-attachment-chain conveyor, an alignment cable loop assembly, and a counterweight assembly contained within a framework.

With the foregoing and other objects in view, there is provided, a whole-body transmission x-ray scanner comprising a collimated x-ray source emitting x-rays, a linear x-ray camera configured to detect the x-rays, a controller, and a positioner that aligns the x-ray source and the x-ray camera to point the emitted x-rays towards the x-ray camera and moves the x-ray source and the x-ray camera synchronously to scan and acquire radiographic images of an object located between the x-ray source and the x-ray camera, the positioner comprising a closed-loop cable alignment assembly fixed to the x-ray source and to the linear x-ray camera to maintain alignment of the x-ray source and the x-ray camera during a scanning mode in which the x-ray source and the x-ray camera move from one end of the object to another end, a motor controlled by the controller, a bi-directional crossover slide track bearing assembly connected to the x-ray source, and a conveyor operatively connected to the motor and to the slide track bearing assembly such that, responsive to actuation of the motor by the controller, the slide track bearing assembly moves in a loop that correspondingly move the x-ray source and the x-ray camera along a single linear axis.

With the objects in view, there is also provided a whole-body transmission x-ray scanner comprises a collimated x-ray source emitting x-rays, a linear x-ray camera configured to detect the x-rays, a controller, and a positioner that aligns the x-ray source and the x-ray camera to point the emitted x-rays towards the x-ray camera and moves the x-ray source and the x-ray camera synchronously to scan and acquire radiographic images of an object located between the x-ray source and the x-ray camera, the positioner comprising a closed-loop cable alignment assembly fixed to the x-ray source and to the linear x-ray camera to maintain alignment of the x-ray source and the x-ray camera during a scanning mode in which the x-ray source and the x-ray camera move from one end of the object to another end, a motor controlled by the controller, a closed-loop, motor-controlled conveyor comprising a first gear operatively connected to the motor, a second gear, and a roller chain wrapped around the first and second gears in a raceway, and a bi-directional crossover slide track bearing assembly connected to the x-ray source and comprising a flange fixed to a point of the roller chain such that, responsive to actuation of the motor by the controller, the roller chain moves in a loop around the first and second gears and the slide track bearing assembly correspondingly moves the x-ray source aligned with the x-ray camera along a single linear axis.

With the objects in view, there is also provided a whole-body transmission x-ray scanner comprising a collimated x-ray source emitting x-rays, a linear x-ray camera configured to detect the x-rays, a counterweight, and a positioner that aligns the x-ray source and the x-ray camera and moves the x-ray source and the x-ray camera synchronously to scan and acquire radiographic images of an object located therebetween, the positioner comprising a cable alignment assembly connecting the counterweight directly to the x-ray source and to the x-ray camera to maintain alignment of the x-ray source and the x-ray camera during a scanning mode in which the x-ray source and the x-ray camera move from one end of the object to another end, a motor, a bi-directional crossover slide track bearing assembly connected to the x-ray source, and a conveyor operatively connected to the motor and to the slide track bearing assembly to move the slide track bearing assembly in a loop that correspondingly translates the x-ray source and the x-ray camera along a single linear axis.

In accordance with another feature, the x-ray source comprises a collimator defining a slit to collimate the x-rays into a narrow fan beam of x-rays and the linear x-ray camera comprises a linear array of photodiodes and is positioned to detect the fan beam of x-rays emitted from the collimator of the x-ray source throughout movement of the x-ray source along the axis.

In accordance with a further feature, the controller is an operator-controlled computer having a user interface with controls to start and stop the scanning mode and, during the scanning mode, create a scanned transmission x-ray image of the object disposed between the x-ray source and the x-ray camera responsive to scanning the x-rays across the object.

In accordance with an added feature, the controller has a selectable manual x-ray scanning mode and a continuous x-ray scanning mode.

In accordance with an additional feature, the computer forms and displays the scanned transmission x-ray image of the object on a display.

In accordance with yet another feature, the manual x-ray scanning mode comprises different manual scanning modes that selectively control movement speed of the x-ray source and the x-ray camera during movement along the axis to alter an x-ray dose for different sizes of the object being scanned.

In accordance with yet a further feature, the controller comprises a dosimeter adjacent the x-ray camera and detecting the x-rays emitted and is configured to drive the conveyor with the motor at a variable speed automatically adjustable to control the x-ray dose through thinner or thicker areas of the object being scanned.

In accordance with yet an added feature, the continuous x-ray scanning mode continuously drives the motor to continually move the x-ray source and the x-ray camera and the controller is configured to start x-ray emissions from the x-ray source when the x-ray camera is at approximately the top of the axis and to stop x-ray emissions when the x-ray camera is at approximately the bottom of the axis.

In accordance with yet an additional feature, the controller displays an x-ray-on indicator while the x-rays are emitted and the controller displays an x-ray-off indicator when the x-rays are not emitted.

In accordance with again another feature, the closed-loop cable alignment assembly remains in constant tension to move the linear x-ray camera in a synchronous motion that retains alignment of the x-rays with the x-ray camera.

In accordance with again a further feature, the conveyor is a closed-loop, motor-controlled conveyor belt system comprising a first gear operatively connected to the motor, a second gear, and a roller chain wrapped around the first and second gears in a raceway, and the slide track bearing assembly comprises a flange fixed to a point of the roller chain such that, responsive to movement of the roller chain around the first and second gears, the slide track bearing assembly moves the x-ray source and the x-ray camera along the axis.

In accordance with again an added feature, the first gear is one of directly and indirectly connected to the motor.

In accordance with again an additional feature, the single linear axis is one of a vertical axis, a horizontal axis, and changeable between the vertical axis and the horizontal axis.

In accordance with still another feature, the object is a person.

In accordance with still a further feature, there is provided a counterweight assembly connected to at least one of the x-ray source, the x-ray camera, and the cable alignment assembly to balance a load of the x-ray source and the x-ray camera so that, when the x-ray source and x-ray camera move along the axis together, they present the same resistance to the motor in either direction along the axis to reduce load-stress on the motor.

In accordance with still an added feature, the motor rotates in a single direction during the scanning mode.

In accordance with still an additional feature, the positioner comprises a slide-track assembly comprising a support tower connected to the conveyor, a track assembly connected to the x-ray camera, and a platform disposed between the x-ray source and the x-ray camera on which the object rests during an x-ray scan.

In accordance with another feature, there is provided a housing surrounding the motor, the slide track bearing assembly, and the conveyor, and at least a portion of the positioner and defining a passageway in which the object enters and exits the housing.

In accordance with another feature, the x-ray source and the x-ray camera move in an x-ray plane and the raceway of the roller chain is in one of a plane parallel to the x-ray plane and a plane orthogonal to the x-ray plane.

In accordance with still a further feature, there is provided a controller operatively connected to the motor such that, responsive to actuation of the motor by the controller, the slide track bearing assembly moves in the loop, the controller being an operator-controlled computer having a user interface with controls to start and stop the scanning mode and, during the scanning mode, create a scanned transmission x-ray image of the object disposed between the x-ray source and the x-ray camera responsive to scanning the x-rays across the object.

In accordance with still an added feature, the controller comprises a dosimeter adjacent or within the x-ray camera, the dosimeter configured to detect the x-rays emitted and drive the conveyor with the motor at a variable speed automatically adjustable to control the x-ray dose through thinner or thicker areas of the object being scanned.

In accordance with still an additional feature, the cable alignment assembly remains in constant tension to move the linear x-ray camera in a synchronous motion that retains alignment of the x-rays with the x-ray camera.

In accordance with another feature, the counterweight balances a load of the x-ray source and the x-ray camera so that, when the x-ray source and x-ray camera move along the axis together, they present the same resistance to the motor in either direction along the axis to reduce load-stress on the motor.

In accordance with another feature, the positioner comprises a support tower connected to the conveyor, a track assembly connected to the x-ray camera, and a platform disposed between the x-ray source and the x-ray camera on which the object rests during an x-ray scan.

In accordance with a concomitant feature, there are provided sensors configured to determine whether the x-ray camera is aligned with the x-ray source, the sensors selected from at least one of transmitters, receivers, and transceivers, the transmitters selected from at least one of an LED, an x-ray beam, and a laser and the receivers selected from at least one of a photodiode and a laser diode.

Although the systems, apparatuses, and methods are illustrated and described herein as embodied in a whole-body transmission x-ray scanner and methods for whole-body scanning, they are, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 15 is a fragmentary, side elevational view of another exemplary embodiment of a vertical indexing-attachment-chain conveyor and bi-directional crossover slide-track assembly for moving the x-ray source with a flange centrally disposed in the vertical indexing-attachment-chain conveyor and moving downwards;

FIG. 16 is a fragmentary, side elevational view of the vertical indexing-attachment-chain conveyor and bi-directional crossover slide-track assembly of FIG. 15 moving the flange upwards;

FIG. 19 is a fragmentary, side elevational and partially cross-sectional view of an exemplary embodiment of a vertical scanning x-ray system having towers, an alignment cable loop assembly, counterweight assemblies, and a conveyor assembly that move an x-ray source and an x-ray camera in alignment with one another;

FIG. 20 is a side elevational view of a tower of FIG. 19; and

DETAILED DESCRIPTION OF THE EMBODIMENTS

Figure 1:
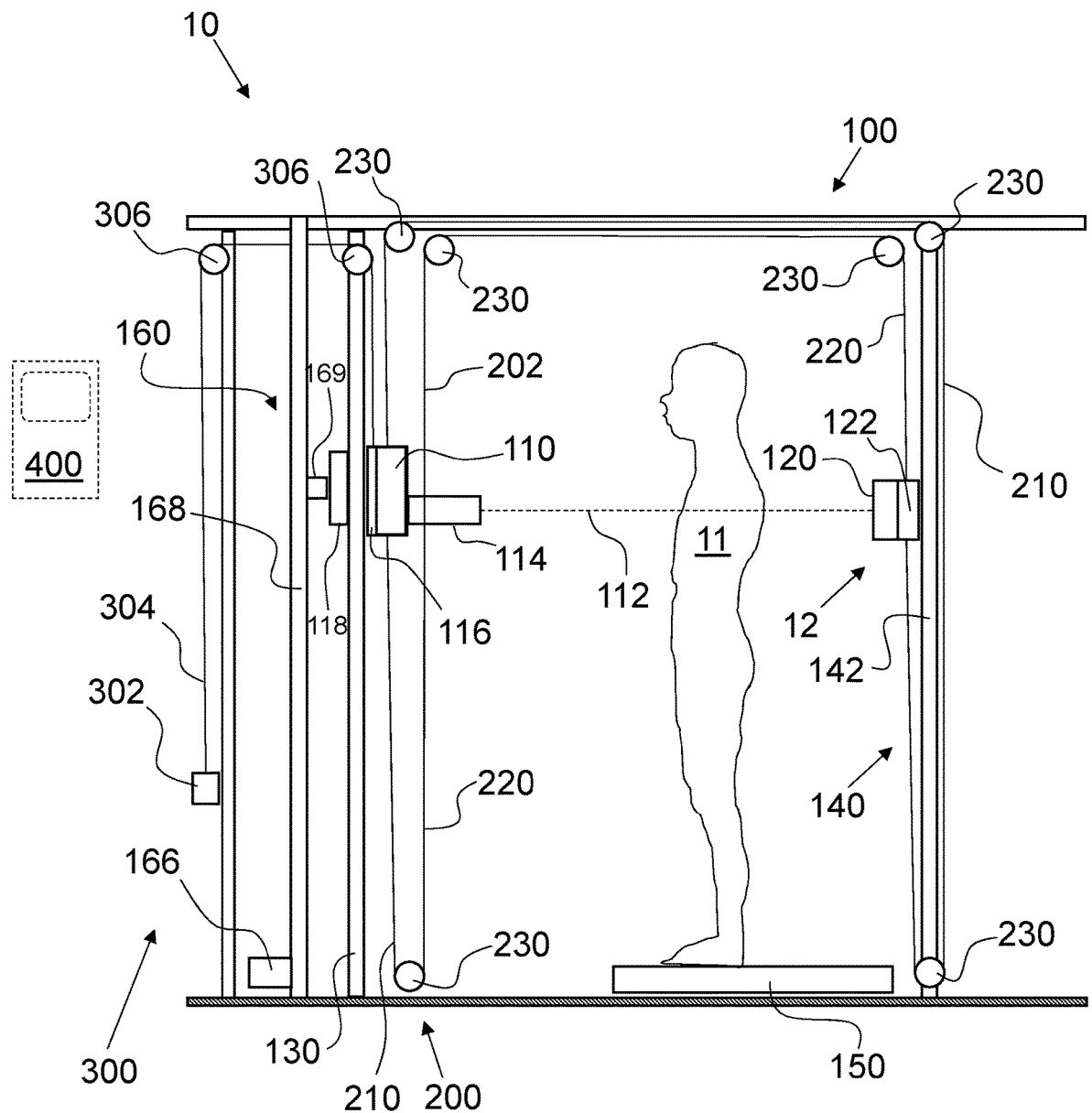
FIG. 1 is a fragmentary, side elevational and partially cross-sectional view of an exemplary embodiment of a vertical scanning x-ray system having an alignment cable loop assembly, a counterweight assembly, and a vertical indexing-attachment-chain conveyor and bi-directional crossover slide-track assembly that move an x-ray source and an x-ray camera in alignment with one another.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

It will be appreciated that embodiments of the systems, apparatuses, and methods described herein may be comprised of one or more conventional processors and unique stored program instructions that control the one or more processors to implement, in conjunction with certain non-processor circuits and other elements, some, most, or all of the functions of the systems, apparatuses, and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIG. 1, there is shown a first exemplary embodiment of vertical scanning x-ray system 10 comprising a bi-directional crossover slide-track assembly 100 and a positioner comprising a closed-loop, vertical indexing-attachment-chain conveyor 160, an alignment cable loop assembly 200, and a counterweight assembly 300. The slide-track assembly 100 moves an x-ray source 110 and a linear x-ray camera 120 with the cable loop assembly 200. The slide-track assembly 100 comprises vertical support towers or rails 130, a vertical track assembly 140 for the x-ray camera 120, and a platform 150 located between the towers 130 and the vertical track assembly 140. The platform 150 is elevated to provide a top surface at a height above ground sufficient to allow the x-ray beam 112 to pass entirely through the feet of a person standing on the platform 150. The cable loop assembly 200 comprises a closed-looped cable 202 having a portion defined as an outer cable 210 and a portion defined as an inner cable 220 for reference with FIG. 1. The outer cable 210 is connected to a mounting plate 116 of the x-ray source 110 and the inner cable 220 is connected to a mounting plate 122 of the x-ray camera 120 through a plurality of pulleys 230. The configuration of the portions 210, 220 of the cable 202 attached to the mounting plates 116, 122 and the pulleys 230 keeps the x-ray source 110 and the x-ray camera 120 aligned during scanning movement as described in further detail below. Herein, the terms pulleys, sprockets, and gears are used. These terms are understood to be broadly defined to not be limited to specific mechanical structures and, therefore, these terms are interchangeable where similar mechanical devices can perform the same function.

Movement of the x-ray source 110 occurs with a vertical indexing-attachment-chain conveyor 160 shown diagrammatically in FIGS. 2 to 7. The conveyor 160 comprises a racetrack 162 (e.g., a roller chain) around a pair of sprockets, pulleys, or gears 164 that, together, move the x-ray source 110 up and down when one of the gears 164 is driven by a motor 166. As the x-ray camera 120 is mechanically linked to the x-ray source 110 through the cable loop assembly 200, the x-ray camera 120 also moves up and down, remaining vertically and horizontally aligned with the x-ray source 110 and the x-ray beam 112 generated by the x-ray source 110. In this way, the x-ray beam 112, emitted by the x-ray source 110 and passing through a collimator 114, passes through a stationary, standing person 11 on the platform 150 from the person's feet to the top of their head (or vice versa) in a single pass so that a whole-body transmission x-ray image can be acquired. In an exemplary embodiment, a counterweight assembly 300, comprising a counterweight 302, a counterweight cable 304, and counterweight pulleys 306, is connected to the x-ray source 110 (or to the mounting plate 116) to relieve stress on the motor 166 by offsetting some or all of the weight of the x-ray source 110 and/or the mounting plate 116 of the x-ray source 110. More specifically, the cable 302 is run through two counterweight pulleys 306 and is fixed to the mounting plate 116, which, in turn, is fixed to the x-ray source 110. Alternatively and/or additionally, the counterweight cable 304 is connected to the x-ray camera 120 or to the mounting plate 122 of the x-ray camera 120.

It is noted that the cable loop assembly 200 is depicted as running the cable 202, 210, 220 between the towers 130 and the track assembly 140 over the top of the person 11. In an alternative non-illustrated configuration, the cable 202 can run below the towers 130 and the track assembly 140, and/or the platform 150.

An exemplary embodiment of the x-ray source 110 suitable for security applications (e.g., contraband detection) is a mono-block x-ray generator model number IXS 1650 manufactured by VJ X-Ray. This mono-block x-ray generator can produce x-rays with an energy up to approximately 160 KeV and a tube current up to approximately 8 mA.

The x-ray source 110 has an x-ray emission port (not shown) that produces a conical beam of x-rays with an emission cone angle of up to approximately 40 degrees. The collimator 114 is mounted at the emission port to collimate the conical beam down to a narrow horizontal fan beam of x-rays 112, which is suitable for a linear x-ray camera 120. A fan beam is desired when scanning people to minimize x-ray exposure to the person being scanned. The x-ray camera 120 has individual photodiode detectors in a photodiode array. The detectors are disposed in a plane having a width and a height. The plane is defined as the detector plane. The width of the detectors is substantially equal to a width of the entire photodiode array. The number of rows of detectors along the width can be a single row or it can be a number of parallel rows, depending on the photodiode array used. In another exemplary embodiment, the x-ray camera has at least two series of diode arrays that allow image subtraction and allow dual imaging using a single x-ray beam source. Each diode array has a different scintillator that allows for image subtraction processing. In the exemplary embodiments, a size of the x-ray beam 112 has a height substantially equal to a height of the total rows of the photodiode detectors of the x-ray camera 120. If the detectors are aligned in a single row, the height of the x-ray beam is approximately the height of the photodiode detector. The width of the x-ray beam 112 is substantially equal to a width of the photodiode array of the x-ray camera 120 in the detector plane. The exemplary embodiment of the size of the x-ray beam 112 minimizes the amount of x-ray radiation not impinging on the photodiode detectors. In alternative exemplary embodiments, the x-ray beam 112 can extend outside the field of the photodiode detectors by a pre-set amount.

In an exemplary embodiment where the x-ray source is emitting x-rays when the system is powered on, the collimator 114 has a movable shield that blocks the x-ray beam 112 when x-ray scanning of a subject is not occurring. In an exemplary embodiment of a normal operation, the x-ray source 110 is on when the system is powered on and emits x-rays while powered on but the x-ray source 110 is turned off when the system is idle for approximately 15 minutes. During this normal operation, a lead shutter (or other suitable x-ray shielding material) is moved over an output aperture defined by the collimator 114 to control emission of x-rays that could expose the x-ray camera 120 (or persons in the vicinity of the system) when scanning is not desired.

Figure 2:
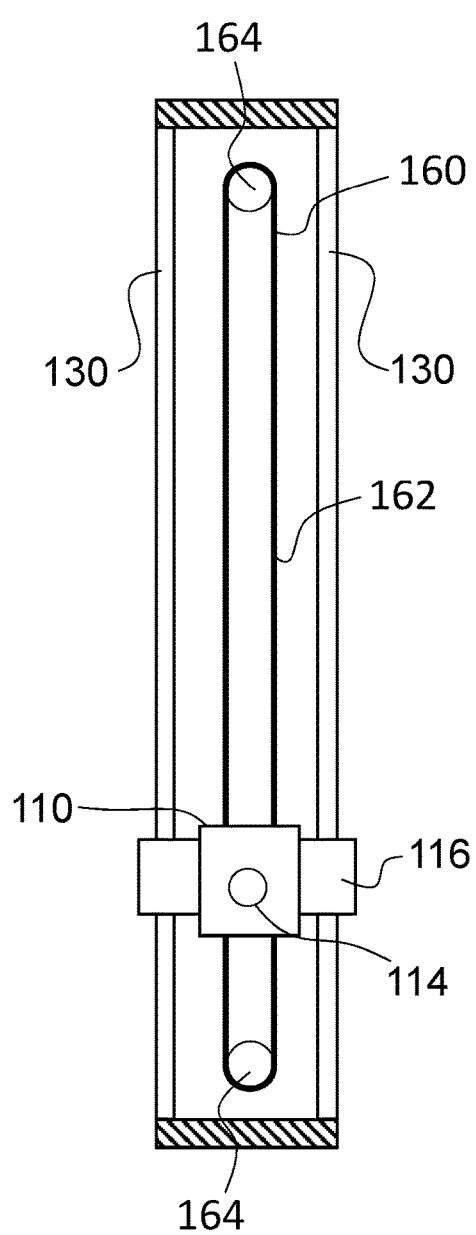
FIG. 2 is a side elevational and partially cross-sectional view of an x-ray source positioning system of the x-ray system of FIG. 1.
Figure 3:
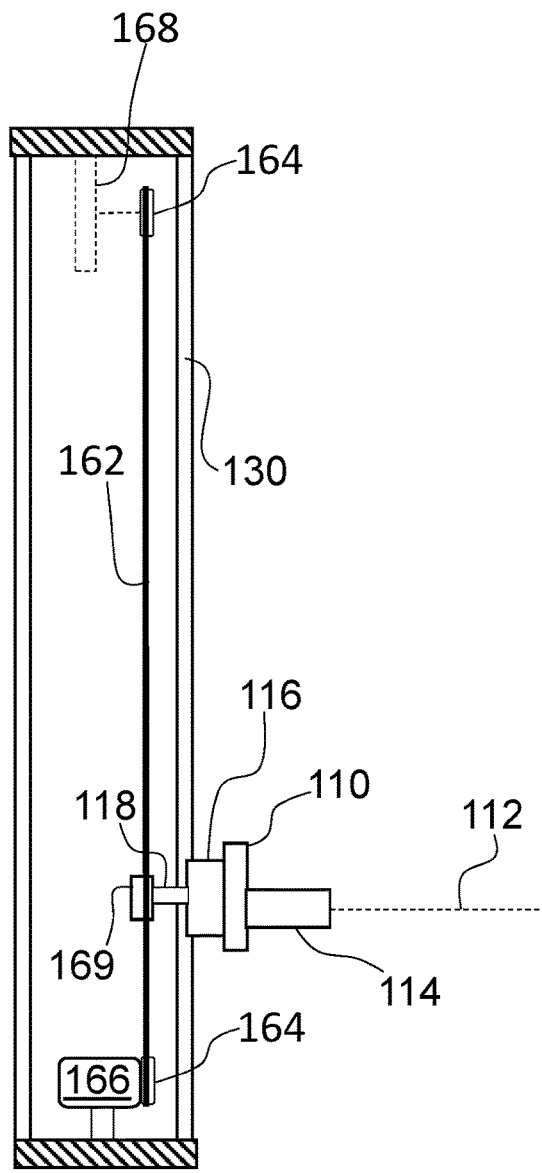
FIG. 3 is a side elevational and partially cross-sectional view of the x-ray source positioning system of FIG. 2 employing a single motor drive attached to a vertical indexing attachment chain conveyor and bi-directional crossover slide track assembly on the x-ray source assembly.
Figures 4, 5:
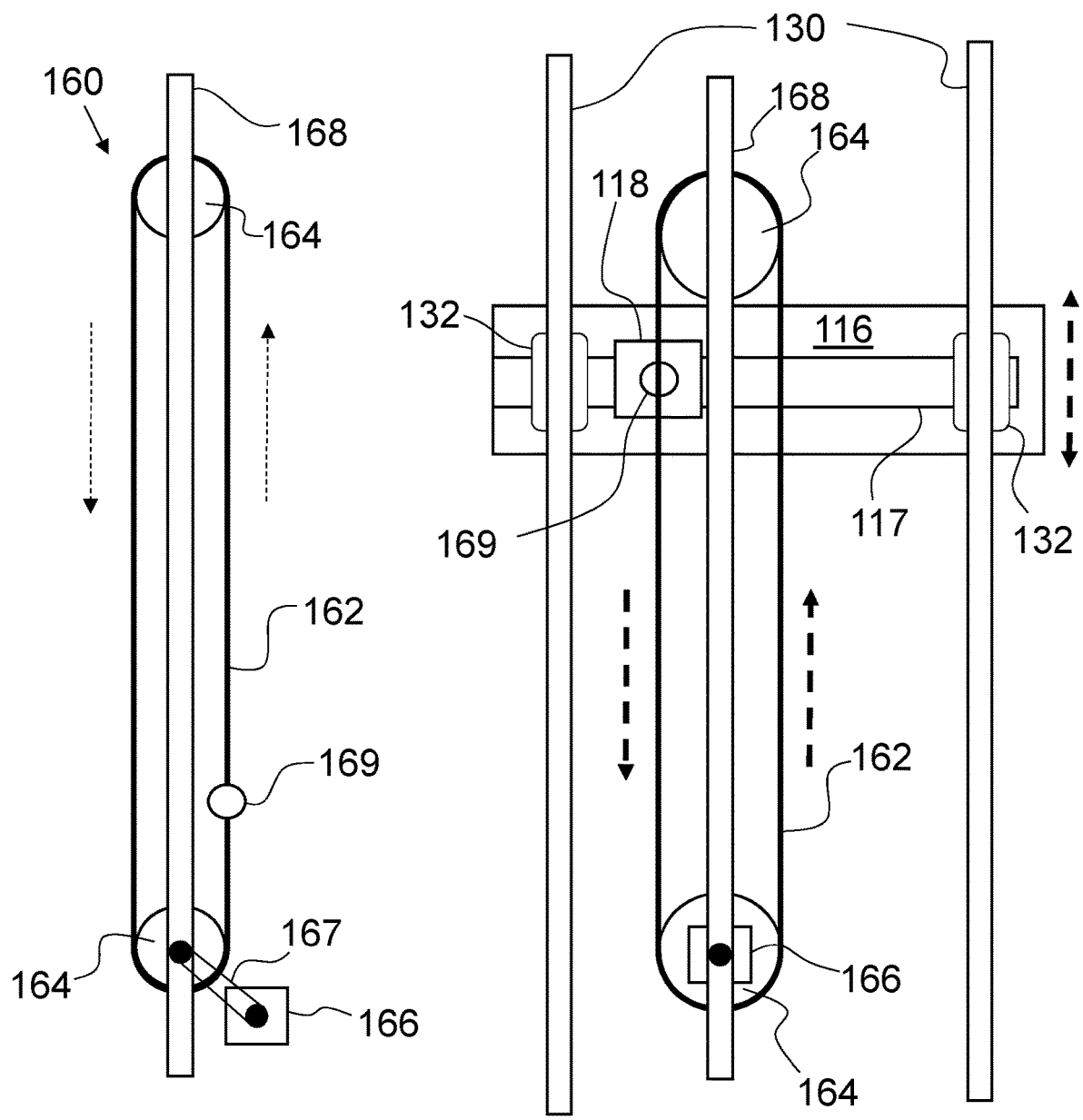
FIG. 4 is a fragmentary side elevational view of a portion of a vertical indexing-attachment-chain conveyor of FIG. 1 with a motor mounted indirectly to the conveyor.
FIG. 5 is a fragmentary, side elevational view of the vertical indexing-attachment-chain conveyor mounted with an x-ray source mounting plate to a support tower and with the motor mounted directly to the conveyor.

Exemplary movement of the x-ray-source 110 is explained first with respect to FIGS. 2 and 3. In this exemplary embodiment, the x-ray source 110 is attached to a center of the x-ray mounting plate 116 (it can be offset vertically or horizontally if desired). The motor 166 is connected to one of the gears 164 of the vertical indexing-attachment-chain conveyor 160, either directly or through a transmission (e.g., a belt, a chain, a drive shaft, and/or a series of gears), each of which are illustrated respectively in FIGS. 4 and 5. The motor 166 in FIG. 5 is a direct drive motor and has an output shaft connected to an axle of the gear 164, in this case a lower gear 164. In contrast, the motor 166 in FIG. 4 is at a distance from the lower gear 164 and the shaft of the motor 166 is connected to an axle of the gear 164 through a transmission such as a belt or drive chain 167. An exemplary embodiment of the motor 166 is a variable-speed gear motor Cyclo 6000 (1-2 hp) manufactured by Sumitomo. Other motors such as servo or stepping motors can be used as well. In another exemplary embodiment, the motor is a variable-speed adjustable motor having the speed controlled by a controller 400. In such a configuration, the x-ray source (and the x-ray camera) can be made to travel faster or slower through a particular part of the scanning area to control the x-ray beam dose, for example, through thinner or thicker areas of the object being scanned. The speed can be adjusted by selecting a preset software application or by using a dosimeter to adjust the speed automatically during the scan. An exemplary embodiment of the vertical indexing-attachment-chain conveyor 160 is a Roller Chain Conveyor manufactured by DirectConveyors.com and is capable of lifting several hundred pounds. The exemplary embodiment of the vertical indexing-attachment-chain conveyor 160 comprises two gears 164, one mounted to the motor 166 and the other mounted on a rigid frame 168, illustrated in FIG. 1 and a portion of which is illustrated in dashed lines in FIG. 3. The roller chain 162 connects the two gears 164 to one another to form a racetrack. Accordingly, when the motor 165 rotates the lower gear 164, the racetrack of the roller chain 162 rotates. Fixed to a given location of the roller chain 162 is at least one bracket or flange 169. The flange 169 is further connected to a slide track bearing assembly 118 that, in turn, is connected to the mounting plate 116 of the x-ray source 110. As such, when the flange 169 moves around the racetrack as the roller chain 162 is driven by the motor 166, the flange 169 moves the slide track bearing assembly 118 up and down (the flange 169 also translates side-to-side approximately equal to a diameter of the gears 164). In other words, the flange 169 moves in a continuous or closed loop, up and down and around the gears 164, as the motor 166 drives the roller chain 162.

Figure 6:
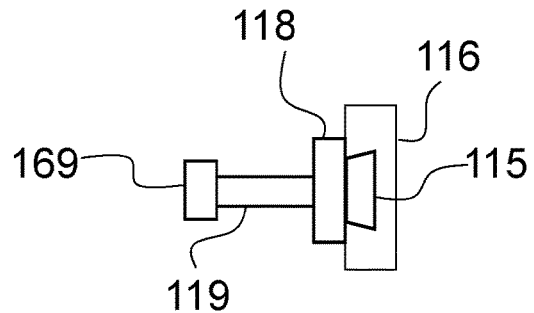
FIG. 6 is a side elevational view of an exemplary embodiment of a connection between an x-ray source mounting plate and the vertical indexing-attachment-chain conveyor with a dovetail joint.

To not impart the same horizontal translation of the flange 169 to the x-ray source 110 as the flange 169 moves from one side of the gears 164 to the other side, the slide track bearing assembly 118 is horizontally movably connected to the mounting plate 116 of the x-ray source 110. An exemplary embodiment of this movable connection is illustrated in FIGS. 5 and 6. This movable connection positions a horizontal slot or groove 117 on a side of the mounting plate 116 opposite the x-ray source 110 (e.g., the rear side) and provides the slide track bearing assembly 118 with a fixture that permits translating movement along the slot 117 but not out of or orthogonal to the slot 117. One exemplary embodiment of such a connection is a dovetail joint, which allows the slide track bearing assembly 118 to slide horizontally back and forth from one side of the gears 164 to the other as the flange 169 (along with the slide track bearing assembly 118) rotates around the gears 164 at both ends of travel around the loop of the roller chain 162. FIG. 6 shows an exemplary embodiment of the flange-to-dovetail-joint connection. The flange 169 is fixed to a first side of the slide track bearing assembly 118 by a rod or bolt 119. The second side of the slide track bearing assembly 118 has a dovetail insert 115. In the exemplary embodiment shown in FIG. 5, the groove 117 in the mounting plate 116 for the dovetail joint is open only on one end (to the left in FIG. 5). Instead of one blind end as illustrated, the other end also can be open. Either or both open ends of the dovetail joint can be closed by fixing a removable spacer (not illustrated). The mounting plate 116 is movably attached to the vertical towers 130 with respective bearings 132 that allow the mounting plate 116 to move vertically along the towers 130 but remain laterally fixed in position with respect to the towers 130. For example, the towers 130 can be rods and the bearings 132 can be hollow pipes each respectively surrounding one of the rods. In this regard, the mounting plate 116 remains precisely positioned both vertically and laterally as it is driven up and down by the flange 169. In the embodiment of FIGS. 1 to 5, the towers 130 are mounted in a plane that is parallel to a plane defined by the raceway of the roller chain 162. In FIG. 5, for example, the plane of the towers 130 is in front of and parallel to the plane of the raceway of the roller chain 162, which can be seen by the connection of the slide track bearing assembly 118 in FIG. 6.

Figure 7:
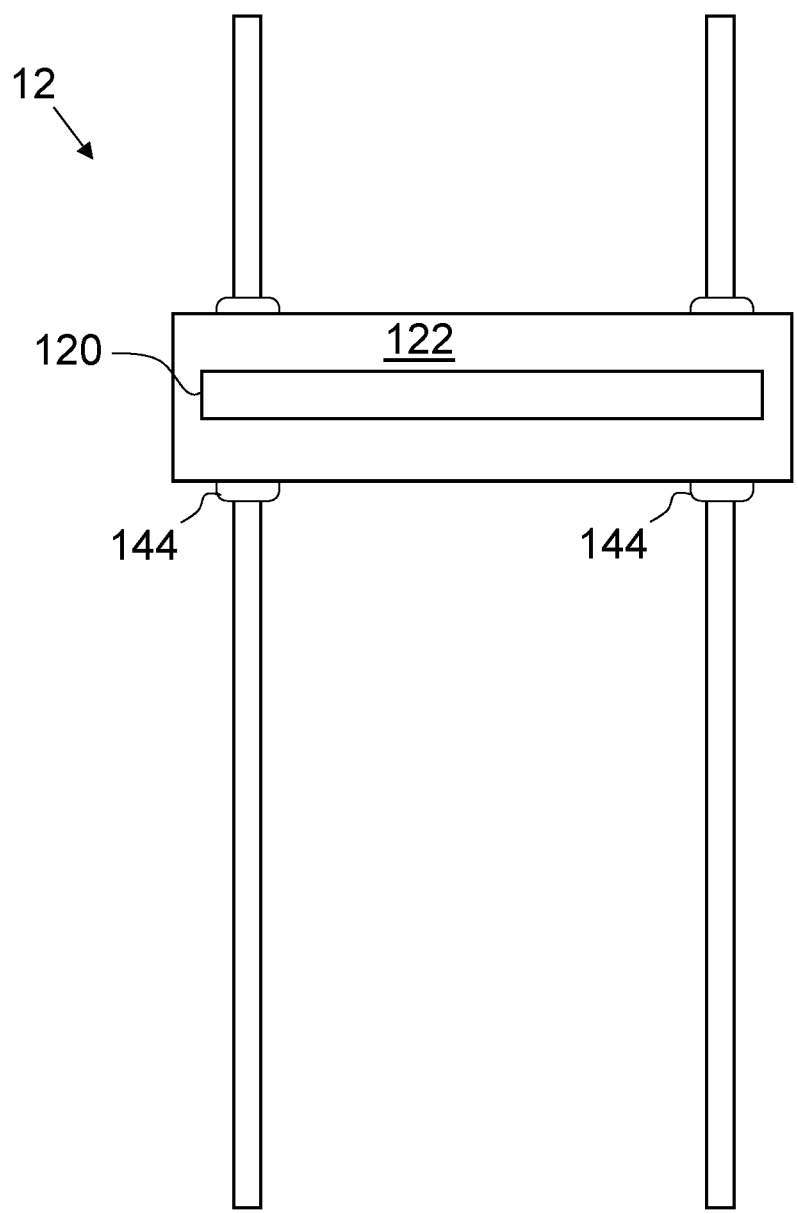
FIG. 7 is a fragmentary, side elevational view of a portion of an exemplary embodiment of the linear x-ray camera of FIG. 1 mounted to a vertical track assembly and a camera mounting plate.

A linear x-ray camera mounting system 12 is shown in FIG. 7. The x-ray camera 120 is attached to the mounting plate 122 so that its linear array of photodiodes faces the x-ray source 110 and is exposed to the narrow fan-beam of x-rays 112. The mounting plate 122 is movably attached to a set of vertical support posts 142 of the vertical track assembly 140 with a set of bearings 144. The respective bearings 144 allow the mounting plate 122 to move vertically along the support posts 142 but remain laterally fixed in position with respect to the support posts 142. For example, the support posts 142 can be rods and the bearings 144 can be hollow pipes each respectively surrounding one of the rods. In this regard, the mounting plate 122 remains precisely positioned both vertically and laterally as it is driven up and down by the cable 202. An example of the linear x-ray camera 120 that is suitable for security applications (e.g., contraband detection) is linear photodiode array model number XI8800-042-DR manufactured by X-Scan Corporation in San Jose, Calif. This camera has a single array of photodiodes each with an active area of 1.6 mm×2.4 mm. The length of the linear array in accordance with an exemplary embodiment is 42 inches (106.7 mm) long. A pixelated scintillator made from Cesium Iodide doped with Thallium is attached to the photodiode array with a thickness of 4 mm. The scintillator material absorbs x-rays that have passed through the body of the subject with high efficiency and converts the absorbed x-rays into a multitude of visible light photons that expose each individual photodiode detector to which it is attached. Each individual photodiode in the diode array has its own block (with a dimension of 1.6 mm×2.4 mm×4 mm) of scintillator material that is separated by a thin layer of opaque material so that light emitted from each block of scintillator material is confined to the photodiode to which it is attached. The length (nominally 0.9 to 1.07 meters) of the linear array is needed to span the entire width of the narrow fan beam of x-rays 112 emitted by the x-ray source 110 when the source-to-camera distance is approximately six feet and the cone angle is forty degrees. In this example of the linear photodiode array, therefore, the size of the x-ray beam 112 will have a height of no more than approximately 1.6 mm and width of no more than approximately 42 inches.

Figure 8:
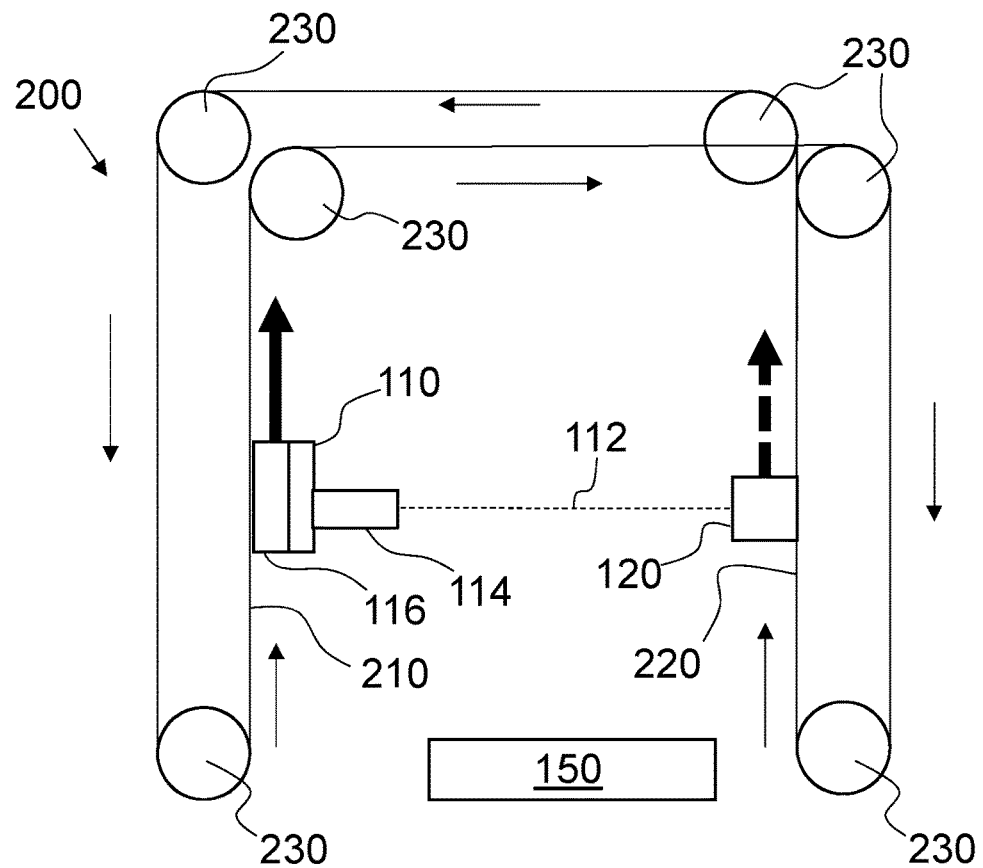
FIG. 8 is a simplified schematic diagram of an exemplary embodiment of the cable loop assembly of the x-ray scanner of FIG. 1 lifting the x-ray source and x-ray camera in alignment with one another.
Figure 9:
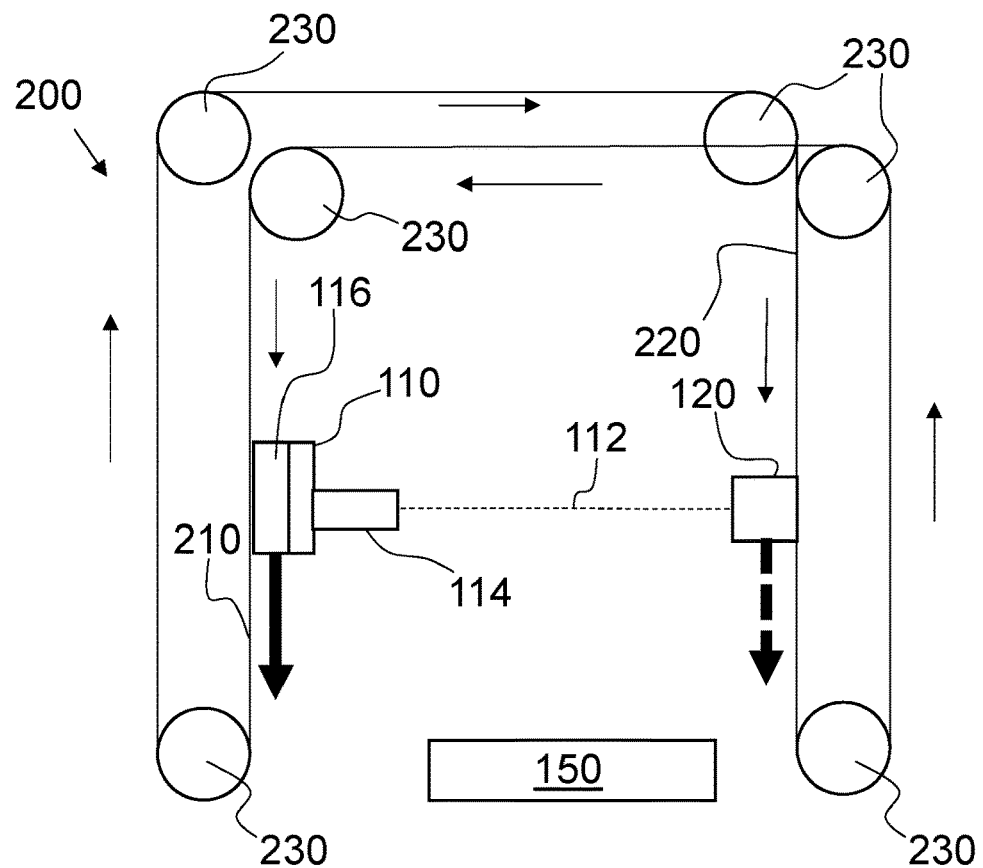
FIG. 9 is a simplified schematic diagram of an exemplary embodiment of the cable loop assembly of the x-ray scanner of FIG. 1 lowering the x-ray source and x-ray camera in alignment with one another.

Referring now to FIGS. 8 and 9, the cabling system is shown without the supporting structure and with the pulleys 230 in a simplified configuration as compared to FIG. 1 for reasons of clarity. As in FIG. 1, the cable loop assembly 200 is guided around the pulleys 230 to form a single raceway. The mounting plate 116 of the x-ray source 110 is fixed to the outer cable 210 (see FIG. 1) and the x-ray camera 120 is fixed to the inner cable 220 (see FIG. 1). With the conveyor 160 driving the x-ray source 110 as described herein, when the x-ray source 110 is moved upwards as shown with the solid arrow in FIG. 8, the x-ray camera 120 that is positioned directly across from the exit of the collimator 114 is moved correspondingly (dashed arrow) to have the beam of x-rays 112 directly impact the detectors of the photodiode array throughout that upwards movement. Likewise, when the x-ray source 110 is moved downwards as shown by the solid arrow in FIG. 9, the x-ray camera 120 that is positioned directly across from the exit of the collimator 114 is moved correspondingly (dashed arrow) to have the beam of x-rays 112 directly impact the detectors of the photodiode array throughout that downwards movement.

Figure 10:
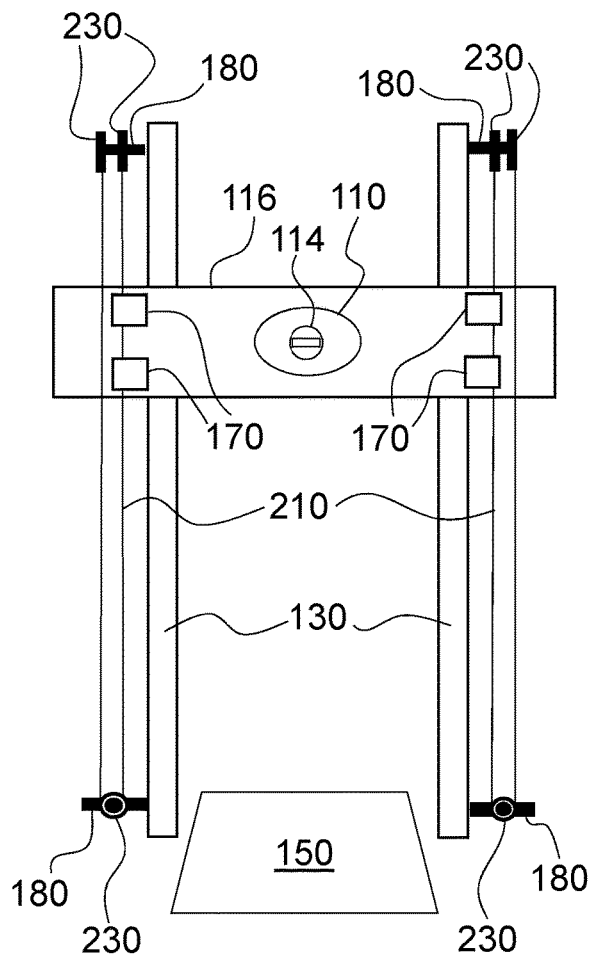
FIG. 10 is a fragmentary, side elevational view of an exemplary embodiment of an x-ray source positioning portion of the x-ray scanner of FIG. 1.
Figure 11:
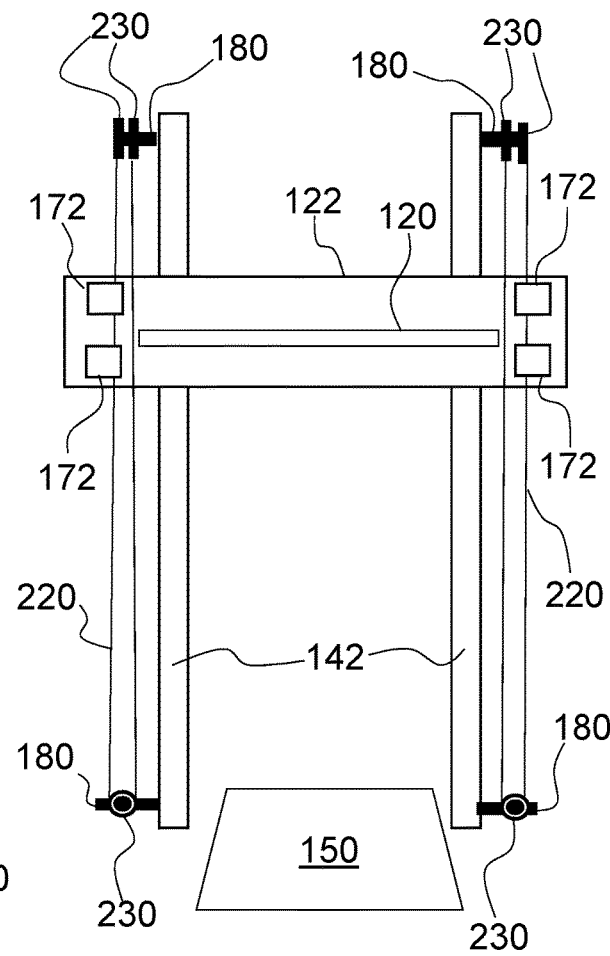
FIG. 11 is a fragmentary, side elevational view of an exemplary embodiment of an x-ray camera positioning portion of the x-ray scanner of FIG. 1.

FIGS. 10 and 11 illustrate how the configuration of the cable loop assembly 200, the pulleys 230, the support towers 130, and the vertical track assembly 140 keep the x-ray source 110 an the x-ray camera 120 aligned at all times. This orientation is from the point of view of the person 11 standing on the platform 150. In FIG. 10, the view is from the person 11 on the platform 150 looking at the x-ray source 110. In this view, the x-ray source 110 and the collimator 114 point directly at the person being scanned. Cable fasteners 170 attach the outer cable 210 to the mounting plate 116 of the x-ray source 110. Support brackets 180 attach the pulleys 230 to the support towers 130. In FIG. 11, the view is from the person 11 on the platform 150 looking at the x-ray camera 120. In this view, the x-ray camera 120 faces the person being scanned. In this view, cable fasteners 172 attach the inner cable 220 to the mounting plate 122 of the x-ray camera 120. Support brackets 180 attach the pulleys 230 to the track assembly 140.

Figure 12:
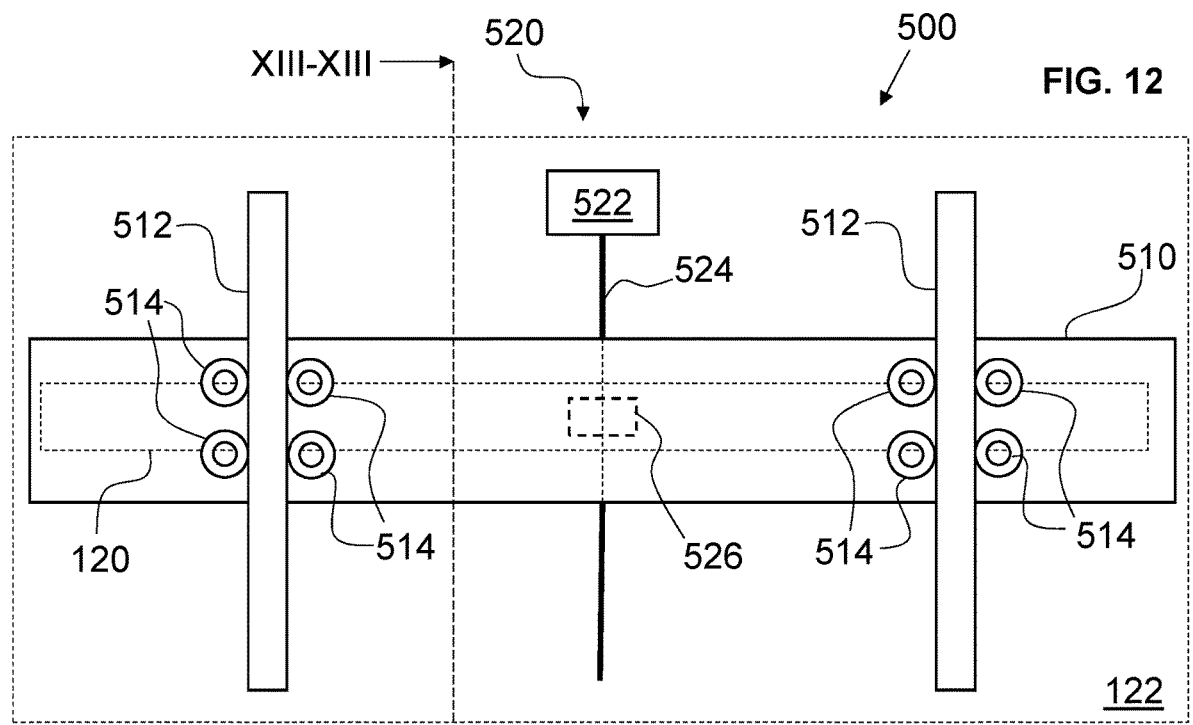
FIG. 12 is a partially hidden, rear elevational view of an exemplary embodiment of a camera fine adjustment assembly.
Figure 13:
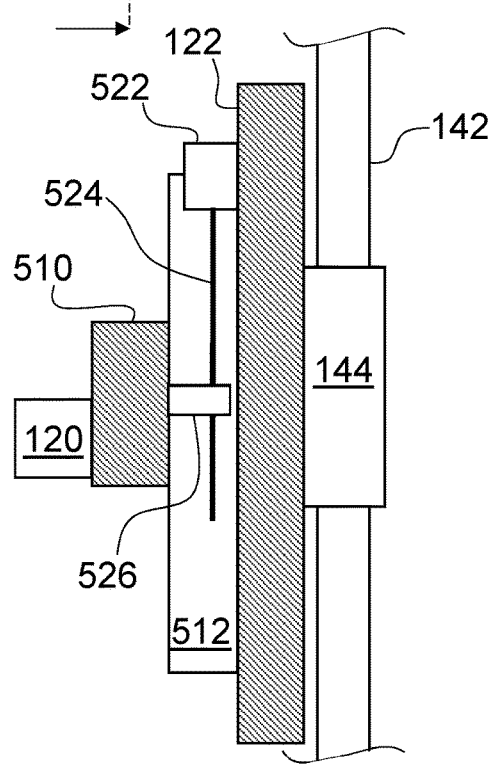
FIG. 13 is a partially cross-sectional, side elevational view of the camera fine adjustment assembly of FIG. 12 along section line XIII-XIII.

Even with precise placement of the camera 120 with respect to the collimator 114, there exists a possibility that the camera 120 and the beam emitted by the collimator 114 become misaligned. To make adjustments after the camera 120 and collimator 114 have been initially aligned, which can be referred to as fine adjustments, a camera adjustment assembly 500 is provided and illustrated in FIGS. 12 and 13. Instead of mounting the x-ray camera 120 directly onto the mounting plate 122, the camera 120 is mounted to the camera adjustment assembly 500, which is, in turn, mounted to the mounting plate 122; in other words, the camera adjustment assembly 500 is sandwiched between the camera 120 and the mounting plate 122. FIG. 12 is a view from a rear side of the camera adjustment assembly 500 that faces the mounting plate 122. Because the mounting plate 122 would block all view of this rear side, the mounting plate 122 is depicted in FIG. 12 with dashed lines. Similarly, because the camera 120 is located on the side of the camera adjustment assembly 500 opposite the mounting plate 122 (in other words, on the far side of a camera mounting plate 510), the camera 120 is illustrated in dashed lines. A partially cross-sectional view of the camera adjustment assembly 500 is depicted in FIG. 13. As can be seen, the bearings 144 (which are movably connected to the vertical support posts 142) are fixed to the mounting plate 122. A pair of camera tracks 512 are fixed to the mounting plate 122. A camera bearing 514 is connected to a respective camera track 512 to be able to move along the camera track 512. As the camera tracks 512 are vertically oriented in this exemplary embodiment, the bearings 514 allow the camera 120 to move vertically with respect to ground (accordingly, a set of horizontal tracks can also be added to or included in the camera adjustment assembly 500). The camera mounting plate 510 is fixed to the bearings 514 such that the camera mounting plate 510 moves with the bearings 514 as the bearings 514 translate along the tracks 512. The camera 120 is fixed to the camera mounting plate 510. In this manner, as the bearings 514 translate along the tracks 512, the camera 120 moves correspondingly.

To control movement of the camera mounting plate 510 with respect to the mounting plate 122, a fine adjustment control assembly 520 comprising a motor 522, a shaft 524, and a gear 526 is provided. In the exemplary embodiment, the motor 522 is fixed to the mounting plate 122. The shaft 524 extends from the motor 522 and rotation of the shaft 524 is controlled and caused by the motor 522. The gear 526 is attached to the camera mounting plate 516 and is operatively connected to the shaft 524 such that, as the shaft 524 rotates, the gear 526 moves along the length of the shaft 524, the gear 526 moving in one direction as the shaft 524 spins in a first direction and moving in an opposite direction as the shaft 524 spins in a second direction opposite the first direction. In an exemplary embodiment, the shaft 524 can be a worm gear shaft and the gear 526 can be a worm gear.

To determine whether the camera 120 is aligned with the x-ray source 110, one or more sensors 530 are mounted on the assembly including the x-ray source and/or the assembly including the x-ray camera. The sensors can include transmitters, receivers, and transceivers. Exemplary embodiments of a transmitter include an LED(s), an x-ray beam(s), and a laser(s) and exemplary embodiments of a receiver include a photodiode(s) and a laser diode(s). During an alignment mode, the source and camera are examined to determine if they are aligned. This can include placing the x-ray source or the x-ray camera at a predetermined position. If the sensor associated with the x-ray camera is aligned with the sensor associated with the x-ray source, then no fine adjustment is required. If the sensor associated with the x-ray camera is not aligned with sensor associated with the x-ray source sensor, then the motor 522 drives the shaft 524 and the gear 526 until the sensor associated with the camera adjustment assembly 500 (including the x-ray camera 120) is aligned with sensor associated with the x-ray source 110. Fine adjustment to align can be achieved in an automatic mode or in a manual mode. The operator can select which mode to use and, in the latter mode, the operator can be provided with a user interface 400 connected to the sensors 530 and displaying an indication when the sensors 530 are in an aligned state and/or in an unaligned state and/or which direction to move the camera adjustment assembly 500 to effect alignment.

Figure 14:
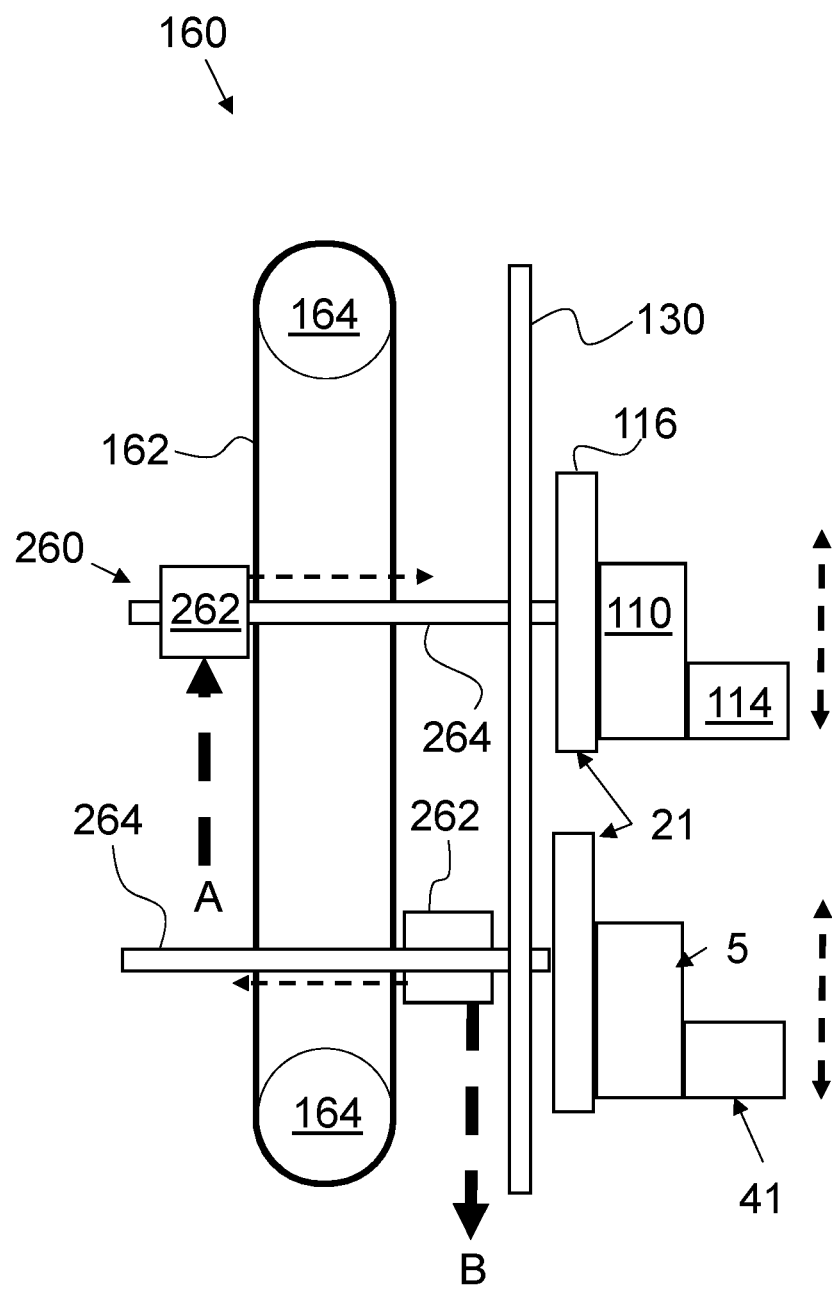
FIG. 14 is a fragmentary, side elevational view of another exemplary embodiment of a bi-directional crossover slide-track assembly in an orientation at an angle to the vertical indexing-attachment-chain conveyor for moving the x-ray source in alignment with an x-ray camera.

FIG. 14 shows another exemplary embodiment of the vertical indexing-attachment-chain conveyor 160. In this configuration, the plane defined by the raceway of the roller chain 162 is perpendicular to the plane defined by the support towers 130. The slide track bearing assembly 118 shown in FIG. 5 connected to the mounting plate 116 is replaced with a slide track bearing assembly 260 having parts, at least one connected to the mounting plate 166 and at least one connected to the roller chain 162. This slide track bearing assembly 260 moves perpendicular to the mounting plate 116, i.e., in the plane of FIG. 14. In this embodiment, a slide track bearing 262 connected to the roller chain 162 is movably disposed on a slide bar 264 that is fixed to the mounting plate 116 and projects away from the side of the mounting plate 116 opposite the x-ray source 110 (e.g., referred to as the rear side). The slide track bearing 262 is connected to the flange 169 on the roller chain 162 at a distance (in other words, the plane of the raceway of the roller chain 162 is parallel to the line defined by the bearing bar 264). As can be seen in the two positions of the x-ray source 110 in FIG. 14 (one upper and one lower), the slide track bearing 262 connected to the roller chain 162 on the left is moving upwards on the racetrack of the conveyor 160 (dashed arrow A) and will move to the right when it travels around the upper gear 164. During this upwards movement, the slide track bearing 262 raises the bearing bar 264 (and the x-ray source 110). As the slide track bearing 262 moves around the upper gear 164, the slide track bearing 262 travels along a horizontal distance. During this time, the slide track bearing 262 slides (to the right) along the bearing bar 264 in the plane perpendicular to the towers 130. During the travel from the upper gear 164 towards the lower gear 164, the slide track bearing 262 moves downwards on the racetrack of the conveyor 160 (dashed arrow B) and lowers the bearing bar 264 (along with the x-ray source 110). When the slide track bearing 262 travels around the lower gear 164, the slide track bearing 262 moves along a horizontal distance (to the left), during which time the slide track bearing 262 slides along the bearing bar 264 to the left in the plane perpendicular to the towers 130.

FIGS. 15 and 16 show yet another exemplary embodiment of the vertical indexing-attachment-chain conveyor 160. In this configuration, the plane of the racetrack formed by the gears 164 and the roller chain 162 is parallel to the planes of the towers 130 and the plane of the mounting plate 116 as in the configuration of FIG. 5. The difference in this configuration from the one in FIG. 5, for example, is that the flange 169 is mounted on the roller chain 2 and projects into the interior of the racetrack and in the plane of the racetrack. The point at which the flange 169 connects to the mounting plate 116 is along a line centered with respect to the roller chain 162 and the gears 164. Along this center line is the rigid frame 168 upon which the gears 164 and the flange 169 are mounted. The frame 168 is fixed with respect to the towers 130 but this fixation structure is not illustrated in these figures. The upper and lower gears 164 are fixed in all three lateral dimensions but are rotationally free with respect to the frame 168 so that the gears 164 can rotate. Accordingly, when the motor 166 rotationally drives, e.g., the lower gear 164, the roller chain 162 moves around the racetrack and rotates the upper gear 164. As a first side/end of the flange 169 is fixed to a point 163 on the roller chain 162, the flange 169 travels around the raceway as the roller chain 162 moves. The other side/end of the flange 169 is fixed to a bearing 134 that is connected to the side of the mounting plate 116 opposite the x-ray source 110 (e.g., referred to as the rear side). This bearing 134 is able to slide up and down the frame 168 between the axles of the gears 164 but is fixed to the inner end of the flange 169 that is opposite the outer end fixed to the roller chain 162. At this inner end, the flange 169 and the bearing 134 are fixed but are rotationally freely connected. Accordingly, motion of the outer end of the flange 169 follows, e.g., the dashed arrows C and D in FIGS. 15 and 16 when the roller chain 162 revolves in a clockwise direction and the motion of the bearing 134 follows the direction of arrows E and F, respectively. The form of the frame 168 between the axles of the gears 164 can take any shape. In one exemplary embodiment, the frame 168 is a rod with a given diameter and the bearing 134 is a rod having an outer diameter larger than the given diameter and having a throughbore with a diameter substantially equal to or slightly larger than the given diameter so that the bearing can translate up and down the rod of the frame 168. Another exemplary embodiment of the frame 168 is a beam having a central vertical slot and of the bearing 134 is a rod having a thickened portion extending to the mounting plate 116, an intermediate, narrowed portion within the central vertical slot, and a thickened head on the other side of the beam of the frame 168. In each of the exemplary embodiments, the flange 169 can rotate with respect to the bearing 134 as it travels around the raceway and the bearing 134 can move vertically up and down along the frame 168 to translate the mounting plate 116 between an uppermost location of the x-ray source 110 (defining a top of a scan) and a lowermost location of the x-ray source 100 (defining a bottom of the scan). It is noted that the frame 168 can be disposed between the plane of the raceway of the roller chain 162 and the plane of the towers 130 or at a side of (to the rear of) the roller chain 162 opposite the mounting plate 116.

Figure 17:
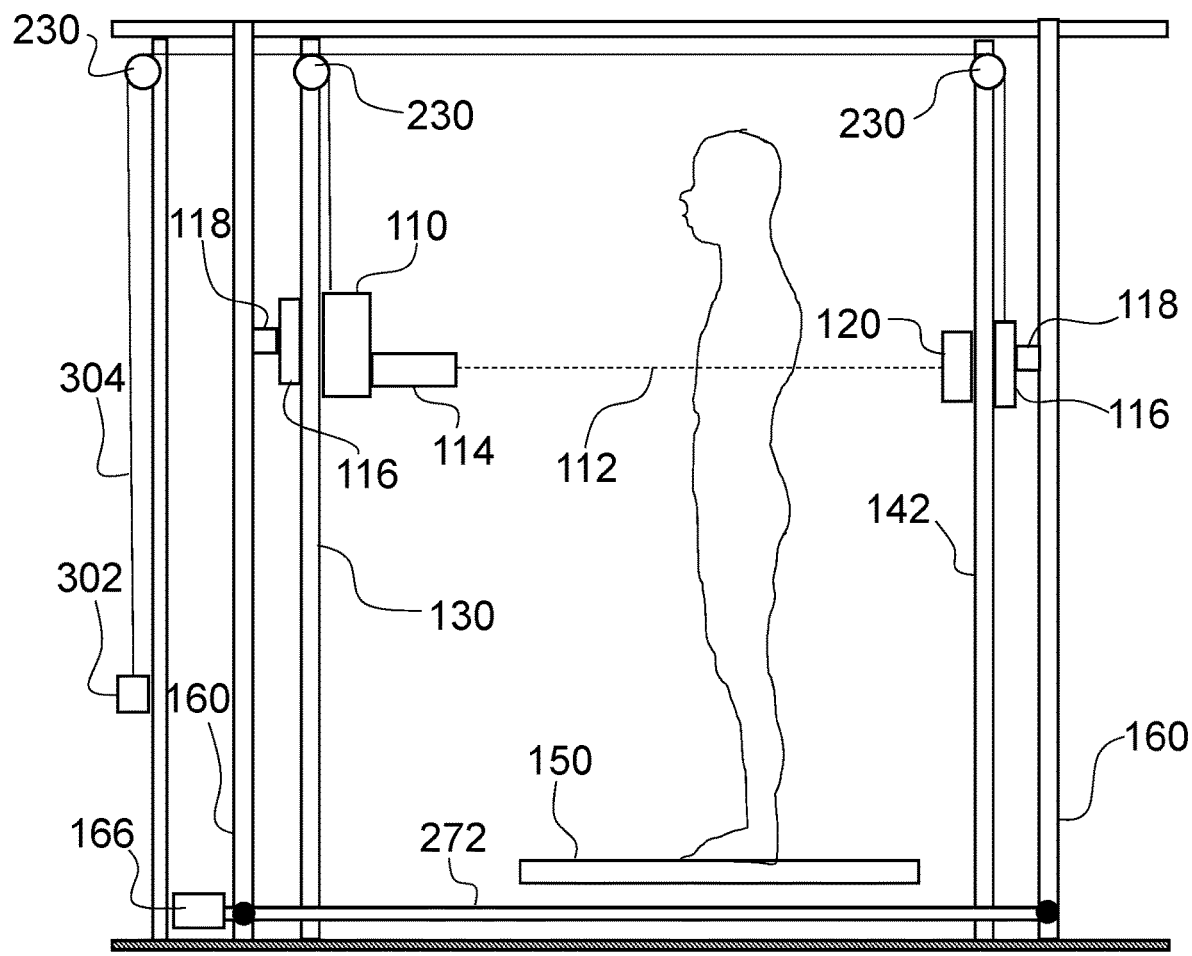
FIG. 17 is a fragmentary, side elevational and partially cross-sectional view of an exemplary embodiment of a vertical scanning x-ray system having a counterweight assembly and drive shaft driven, vertical indexing-attachment-chain conveyors with bi-directional crossover slide-track assembly that respectively move an x-ray source and an x-ray camera in alignment with one another.
Figure 18:
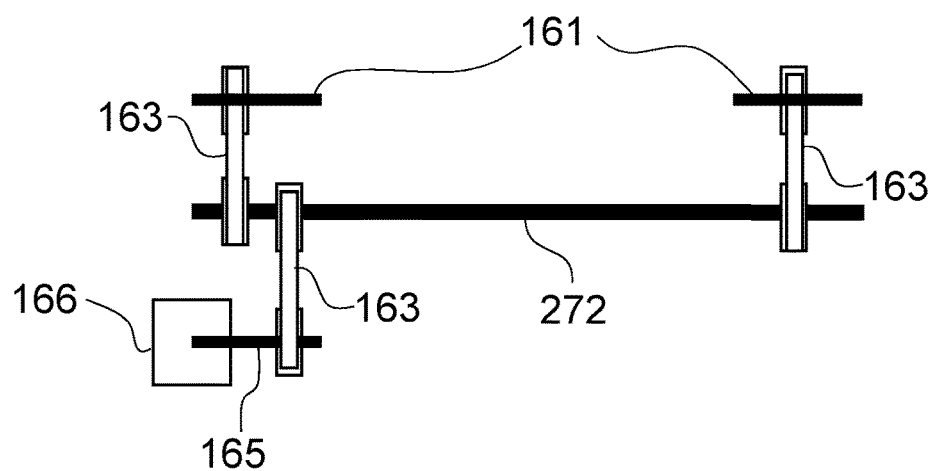
FIG. 18 is a fragmentary, top plan view of an exemplary embodiment of a drive shaft system for the vertical indexing-attachment-chain conveyors of FIG. 17.

FIGS. 17 and 18 illustrate yet another exemplary embodiment of the vertical scanning x-ray system 10. In this exemplary configuration, the x-ray source 110 and the x-ray camera 120 each have their own vertical indexing-attachment-chain conveyors 160 (each with a slide track bearing assembly 118). A single motor 166 drives both of the conveyors 160 through a single drive shaft 272. As shown in the exemplary embodiment of FIG. 18, the output shaft 165 of the motor 166 is connected to a driver 163 (which can be a gear, a transmission, a belt, or any other similar mechanism) that is connected to the drive shaft 272. This drive shaft 272, in turn, is connected through other drivers 163 to respective shafts 161 on the conveyors 160 to rotate the conveyors 160 and move the x-ray source 110 and the x-ray camera 120 together in alignment. Because both conveyors 160 are driven simultaneously with a single drive, the cable loop assembly 200 is no longer needed and, therefore, is not present. In the exemplary embodiment, the drive shaft 272 is connected directly to the conveyors 160. Alternatively, the drive shaft 272 can be connected indirectly through a transmission (e.g., a belt). The x-ray source 110 and the x-ray camera 120 are both moved by the same motor assembly keeping them always aligned during scanning procedures.

In another exemplary embodiment, the x-ray scanner comprises a second x-ray source and a second linear x-ray camera that is installed ninety degrees from the first x-ray source and the first linear x-ray camera to create a 3D simulation image. The second x-ray source and the second x-ray camera are controlled by the same motor drive as the first x-ray source and first linear x-ray camera and additional alignment cables are added to drive the second x-ray source and second x-ray camera.

FIGS. 19 and 20 illustrate a further exemplary embodiment of a counterweight assembly for the vertical scanning x-ray system 10. This configuration has two support towers 600, each tower 600 being, for example, approximately 12" wide×8" deep×94" high. The towers 600 in this embodiment are hollow and rectangular and are made of, for example, steel or aluminum. The x-ray source 110 is mounted on a source mounting assembly 610 movably connected to a first of the towers 600 such that the source 110 can move vertically along the first tower 600 and the x-ray camera 120 is mounted on a camera mounting assembly 620 movably connected to a second of the towers 600 such that the camera 120 can move vertically along the second tower. These movable connections can take any form described herein and are not repeated here but are incorporated herein by reference. An exemplary embodiment for such a connection comprises bearings 612, 622 on each of the source mounting assembly 610 and the camera mounting assembly 620 and a vertical track 602 at each tower 600. A respective one of the source mounting assembly 610 and the camera mounting assembly 620, therefore, rides with the bearings 612, 622 on the track 602.

The source mounting assembly 610 and the camera mounting assembly 620 are operatively connected together so that the source 110 and the camera 120 move vertically together as described in various embodiments herein. These embodiments are not repeated again but are incorporated herein by reference. In the exemplary embodiment shown in FIG. 19, the movable connection between the source mounting assembly 610 and the camera mounting assembly 620 is an alignment cable loop assembly 200 comprising a cable 202 and set of pulleys 230. With a fixed connection of the cable 202, therefore, any vertical movement of one of the camera 120 or the source 110 results in a corresponding vertical movement of the other while keeping the two aligned (if mounted horizontally, then the corresponding movement is horizontal). In this exemplary embodiment, controlled movement of the source 110 is carried out by a conveyor assembly 160 that can be of any form described herein, which forms are not repeated here but are incorporated herein by reference. This exemplary embodiment includes a motor connected to a conveyor, which conveyor is connected to a bearing that is connected to the source mounting assembly 610.

In comparison to the device of FIG. 1, having one counterweight 301, in FIGS. 19 and 20, each tower 600 includes a separate counterweight 630. These counterweights 630 are internal to each tower 600 and are connected respectively to the source mounting assembly 610 and the camera mounting assembly 620 by counterweight cables 632. Accordingly, as either of the source mounting assembly 610 or the camera mounting assembly 620 moves, the respective counterweight 630 moves, as shown by the dashed arrows in FIG. 19.

The embodiments of the vertical scanning x-ray systems and methods described and shown herein are illustrated without any housing. In use, these scanners can be enclosed with walls and appropriate covers that define a passageway through which each subject to be scanned will enter and exit the scanning area over the platform 150. The covers can be configured to allow the subject to enter the passageway in a single direction and exit in another (e.g., opposite) direction or they can be configured to allow the subject to enter and exit the scanning area in the same direction. The covers can be x-ray opaque in various locations to inhibit or prevent stray x-ray radiation from escaping the housing.

Control of the scanning can occur with controller 400 having at least one processor. The Controller is illustrated diagrammatically in FIG. 1. The controller 400 has a user interface connected to the at least one processor to allow operators, for example, to register persons being scanned into a database and to control any and all aspects of the x-ray source 110, the linear x-ray camera 120, the collimator 114, and the motor 166 to acquire images and display those images for analysis. A personal computer can be used as the processor and/or user interface with at least one controlling software application. The x-ray source 110 and the x-ray camera 120 have communication ports, such as USB or serial ports (RS-232), so that they can be controlled from the computer program. Motor controllers (e.g., the processor(s)) can be used to provide remote control, through a computer interface, to almost any type of motor commercially available.

In accordance with another exemplary embodiment of the scanner, the person being imaged can lay horizontally on a table instead of standing on a platform. In such a case, the positioning system is rotated ninety degrees from that shown and described herein so that the x-ray source 110 moves laterally in a plane parallel to the table top and the x-ray camera 120 moves underneath the table top. The supporting tower 130 and track assembly 140 are, then mounted in a fixed horizontal plane that does not need a counterweight assembly. In another exemplary configuration, the supporting tower 130, the track assembly 140, and the cable loop assembly 200 could be mounted in a structure that is rotated from a person-standing position (i.e., vertical) to a lay-down position (i.e., horizontal).

In accordance with yet another exemplary embodiment of the scanning x-ray system, the vertical indexing-attachment-chain conveyor 160 is mounted horizontally and the track assembly 140 is mounted horizontally. In this configuration, the x-ray source 110 produces a vertical fan beam of x-rays that is further collimated into a narrow fan beam of x-rays 112 oriented vertically that sweeps laterally back and forth. Correspondingly, the linear x-ray camera 120 is also rotated to a vertical position. The cable loop assembly 200 along with the support rails 130 and track assembly 140 are also mounted horizontally to allow the x-ray source 110 and the x-ray camera 120, respectively, to pan laterally across a stationary object or person. The x-ray camera 120 in this configuration is long enough to capture an image of an entire person, in other words, about 80 inches (203 cm) long.

For security screening applications the x-ray source 110 and the x-ray camera 120 as described herein provide suitable exposure dose and image quality. For other applications such as medical diagnostics, the x-ray source 110 increases output power and the x-ray camera 120 has smaller pixel sizes to provide the image quality needed for medical diagnostics. An example of such an x-ray source 110 is one that has a power output in the approximately 10 kW to 50 kW range and the x-ray camera 120 needs a pixel size of greater than or equal to approximately 0.2 mm.

Figure 21:
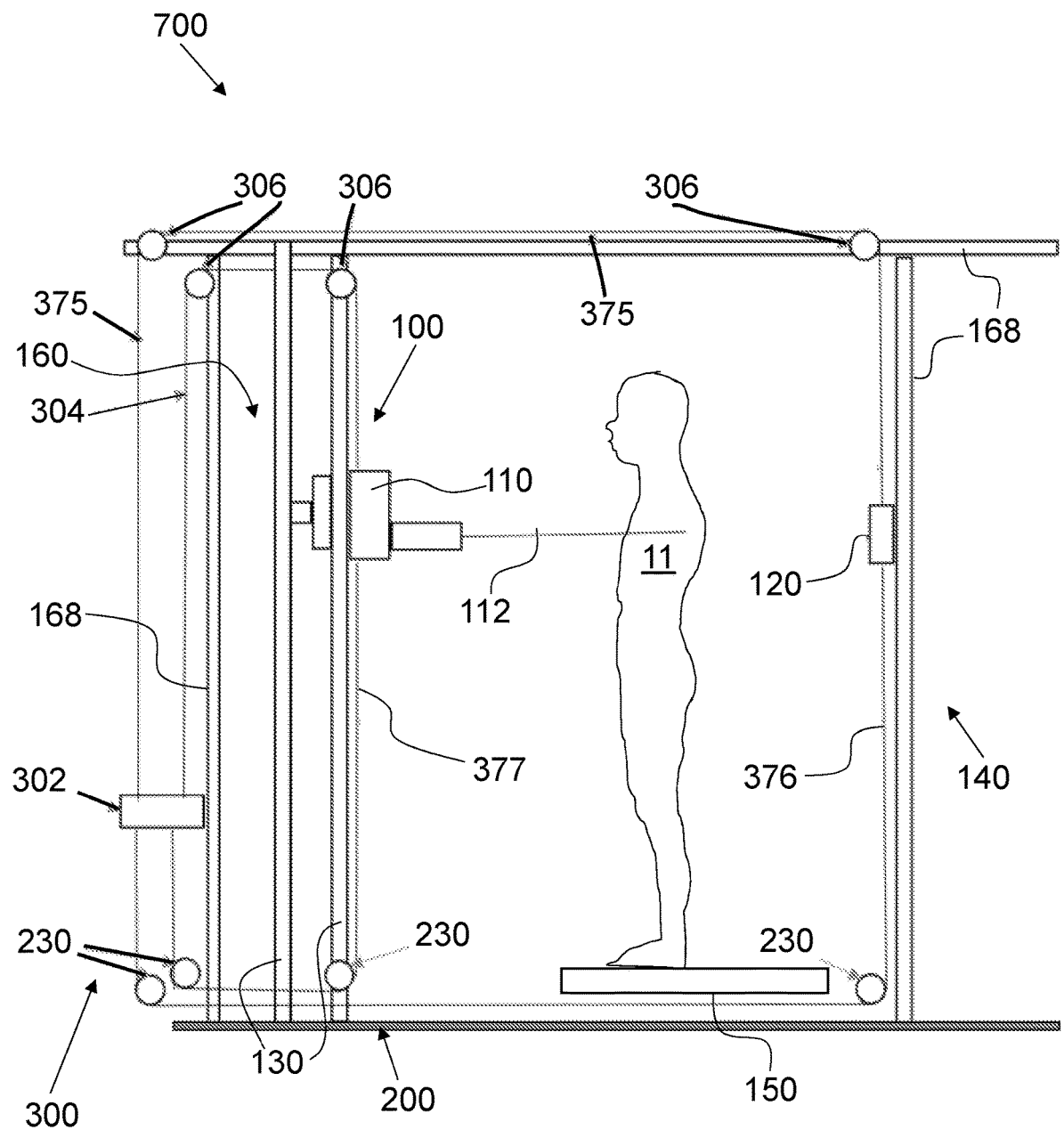
FIG. 21 is a fragmentary, side elevational and partially cross-sectional view of an exemplary embodiment of a vertical scanning x-ray system having an alignment cable loop assembly, a counterweight assembly, and a vertical indexing-attachment-chain conveyor and bi-directional crossover slide-track assembly that move an x-ray source and an x-ray camera in alignment with one another.

Referring now to FIG. 21, there is shown another exemplary embodiment of vertical scanning x-ray system 700 having a closed-loop counterweight assembly and vertical indexing-attachment-chain conveyors with bi-directional crossover slide-track assembly that respectively move an x-ray source and x-ray camera in alignment with one another. This system 700 is different from the system 10 in the exemplary embodiment of FIG. 1. In the system 10 of FIG. 1, a cable 304 is connected from the x-ray source 110 to the counterweight 302. A second cable 220 is connected from the top of the x-ray camera 120 to the bottom of the x-ray source 110. A different cable 210 connects the bottom of the x-ray camera 120 to the top of the x-ray source 110 forming a closed-loop alignment system. In the embodiment of FIG. 21, however, both the x-ray source 110 and the x-ray camera 120 are connected directly to the counterweight 302. As in the previous system, the vertical scanning x-ray system 700 comprises a bi-directional crossover slide-track assembly 100, a positioner comprising a closed-loop, vertical indexing-attachment-chain conveyor 160, an alignment cable loop assembly 200 and a counterweight assembly 300. The bi-directional crossover slide-track assembly 100 and the closed-loop, vertical indexing-attachment-chain conveyor 160 are not described in greater detail with respect to this exemplary embodiment and that description is incorporated herein by reference.

More particularly, with respect to the counterweight assembly 300, a counterweight cable 304 connects the x-ray source 110 to the counterweight 302 (here, from the top of the x-ray source 110 to the top of the counterweight 302) passing around two pulleys 306, which are located in an upper section of a rigid framework 168. A second counterweight cable 377 connects the x-ray source 110 to the counterweight 302 (here, from the bottom of the x-ray source 110 to the bottom of the counterweight 302) passing around two pulleys 230, which are located in a lower section of the framework 168. A third counterweight cable 375 connects the x-ray camera 120 to the counterweight 302 (here, from the top of the x-ray camera 120 to the top of the counterweight 302) passing around two pulleys 306, which are located in the upper section of the framework 168. These two pulleys 306 in this exemplary embodiment are located outside of the two pulleys 306 of the first counterweight cable 304 (with respect to the plane of the drawing of FIG. 21). Finally, a fourth counterweight cable 376 connects the x-ray camera 120 to the counterweight 302 (here, from the bottom of the x-ray camera 120 to the bottom of the counterweight 302) passing around two pulleys 230, which are located in the lower section of the framework 168. These two pulleys, in this exemplary embodiment are located outside of the two pulleys 230 of the second counterweight cable 377 (with respect to the plane of the drawing of FIG. 21). As compared to the system 10 of FIG. 1, therefore, cables 210 and 220 are replaced by cables 375, 376, and 377. In this exemplary embodiment, the closed-loop alignment cable system 700 is more effective in eliminating load imbalance that can cause irregularities in the motion of the system during direction changes at the top and bottom of the vertical indexing-attachment-chain conveyor by creating a constant tension between the x-ray source 110, the x-ray camera 120, and the counterweight 302.

The framework 168 containing the bi-directional crossover slide-track assembly 100, the conveyor 160, the alignment cable loop assembly 200, and the counterweight assembly 300 comprises vertical support towers or rails and a platform 150 located between the vertical towers. The platform 150 is elevated to provide a top surface at a height above ground sufficient to allow the x-ray beam 112 to pass entirely through the feet of a person 11 standing on the platform 150.

Manual Scanning Mode

For manual scanning, the system operates in a single cycle mode. The person is positioned in an x-ray scan position indicated, for example, by an outline image of two feet on the floor at a shoulder width apart. The operator starts the scan from an operator control station. The conveyors start moving and, once the x-ray source and x-ray camera are in a position to start a scan (e.g., at the top of the scanning area), the x-ray beam is engaged and the x-ray scan of the person begins and continues until the source/camera reach a bottom of the scan area, at which time the x-ray beam is turned off. The x-ray source and x-ray camera continue to a home position and stop and do not proceed until the operator starts the next scan. One example of the home position is at the bottom of the conveyor. In this position, the speed of the x-ray source and x-ray camera will be constant by the time that a scan starts from the top of the conveyor and stops at the bottom of the conveyor. Another example of the home position is at a position in the intermediate extent of the conveyor. In this position, the speed of the x-ray source and x-ray camera will be constant by the time that a scan starts from either the top of the conveyor and stops at the bottom of the conveyor or the bottom of the conveyor and stops at the top of the conveyor.

Continuous Scanning Mode

In a continuous scanning mode, the system operates continuously but only allows x-rays to travel to the camera when a person is present in the scanning area. In this mode, at the scan of a first person, the operator has the first person enter the x-ray scanning area and stand in a scanning position, e.g., indicated by images of two feet on the floor. The operator starts the continuous scan mode and follows the manual scanning mode procedures. Once the x-ray scan of that person is complete, that person leaves the scanning area and the next person enters the scanning area, assumes the scanning position, and waits for the scan to begin and end. The system does not park but, instead, continues to operate in this mode until the operator stops the scanning process. In the continuous scanning mode, therefore, the conveyor moves the x-ray source and x-ray camera continuously up and down, e.g., at a constant rate, and each respective person is scanned with x-rays from top-to-bottom or from bottom-to-top.

The system operator can select a manual single scan mode from a menu and, in an exemplary embodiment, select different scanning modes that control the speed of the x-ray source and the x-ray camera for different sizes of people allowing increased x-ray dose for larger persons (slower speed) and lower x-ray dose for smaller persons (faster speed). The system operator also has an option for the continuous scanning mode. As set forth above, in the continuous scanning mode, the system motor drive assembly continues moving and the x-ray scan starts when the x-ray source and the x-ray camera are in start scan position (which can be at the top of the rotation of the conveyor belt/chain). An x-ray-on indicator (e.g., a red light) is illuminated when the x-ray beam is active. Once the scan is complete, the x-ray-on indicator turns off and an x-ray-off indicator (e.g., a green light) is illuminated to allow the person who was just scanned to exit and give time for the next person to be scanned to enter and position themselves before the x-ray-on indicator is illuminated and when x-ray beam reactivates.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A whole-body transmission x-ray scanner, comprising:
a collimated x-ray source emitting x-rays;
a linear x-ray camera configured to detect the x-rays;
a counterweight; and
a positioner that aligns the x-ray source and the x-ray camera and moves the x-ray source and the x-ray camera synchronously to scan and acquire radiographic images of an object located therebetween, the positioner comprising:
  a cable alignment assembly connecting the counterweight directly to the x-ray source and to the x-ray camera to maintain alignment of the x-ray source and the x-ray camera during a scanning mode in which the x-ray source and the x-ray camera move from one end of the object to another end;
  a motor;
  a bi-directional crossover slide track bearing assembly connected to the x-ray source; and
  a conveyor operatively connected to the motor and to the slide track bearing assembly to move the slide track bearing assembly in a loop that correspondingly translates the x-ray source and the x-ray camera along a single linear axis.

2. The scanner according to claim 1, wherein:
the x-ray source comprises a collimator defining a slit to collimate the x-rays into a narrow fan beam of x-rays; and
the linear x-ray camera comprises a linear array of photodiodes and is positioned to detect the fan beam of x-rays emitted from the collimator of the x-ray source throughout movement of the x-ray source along the axis.

3. The scanner according to claim 1, which further comprises a controller operatively connected to the motor such that, responsive to actuation of the motor by the controller, the slide track bearing assembly moves in the loop, the controller being an operator-controlled computer having a user interface with controls to start and stop the scanning mode and, during the scanning mode, create a scanned transmission x-ray image of the object disposed between the x-ray source and the x-ray camera responsive to scanning the x-rays across the object.

4. The scanner according to claim 3, wherein the controller has a selectable manual x-ray scanning mode and a continuous x-ray scanning mode.

5. The scanner according to claim 3, wherein the computer forms and displays the scanned transmission x-ray image of the object on a display.

6. The scanner according to claim 4, wherein the manual x-ray scanning mode comprises different manual scanning modes that selectively control movement speed of the x-ray source and the x-ray camera during movement along the axis to alter an x-ray dose for different sizes of the object being scanned.

7. The scanner according to claim 6, wherein the controller comprises a dosimeter adjacent or within the x-ray camera, the dosimeter configured to detect the x-rays emitted and drive the conveyor with the motor at a variable speed automatically adjustable to control the x-ray dose through thinner or thicker areas of the object being scanned.

8. The scanner according to claim 4, wherein the continuous x-ray scanning mode continuously drives the motor to continually move the x-ray source and the x-ray camera and the controller is configured to start x-ray emissions from the x-ray source when the x-ray camera is at approximately the top of the axis and to stop x-ray emissions when the x-ray camera is at approximately the bottom of the axis.

9. The scanner according to claim 8, wherein the controller displays an x-ray-on indicator while the x-rays are emitted and the controller displays an x-ray-off indicator when the x-rays are not emitted.

10. The scanner according to claim 1, wherein the cable alignment assembly remains in constant tension to move the linear x-ray camera in a synchronous motion that retains alignment of the x-rays with the x-ray camera.

11. The scanner according to claim 1, wherein:
the conveyor is a closed-loop, motor-controlled conveyor belt system comprising:
a first gear operatively connected to the motor;
a second gear; and
a roller chain wrapped around the first and second gears in a raceway; and
the slide track bearing assembly comprises a flange fixed to a point of the roller chain such that, responsive to movement of the roller chain around the first and second gears, the slide track bearing assembly moves the x-ray source and the x-ray camera along the axis.

12. The scanner according to claim 11, wherein the first gear is one of directly and indirectly connected to the motor.

13. The scanner according to claim 11, wherein the x-ray source and the x-ray camera move in an x-ray plane and the raceway of the roller chain is in one of:
a plane parallel to the x-ray plane; and
a plane orthogonal to the x-ray plane.

14. The scanner according to claim 1, wherein the single linear axis is one of:
a vertical axis;
a horizontal axis; and
changeable between the vertical axis and the horizontal axis.

15. The scanner according to claim 1, wherein the object is a person.

16. The scanner according to claim 1, wherein the counterweight balances a load of the x-ray source and the x-ray camera so that, when the x-ray source and x-ray camera move along the axis together, they present the same resistance to the motor in either direction along the axis to reduce load-stress on the motor.

17. The scanner according to claim 1, wherein the motor rotates in a single direction during the scanning mode.

18. The scanner according to claim 1, wherein the positioner comprises a support tower connected to the conveyor, a track assembly connected to the x-ray camera, and a platform disposed between the x-ray source and the x-ray camera on which the object rests during an x-ray scan.

19. The scanner according to claim 1, further comprising a housing surrounding the motor, the slide track bearing assembly, and the conveyor, and at least a portion of the positioner and defining a passageway in which the object enters and exits the housing.

20. The scanner according to claim 1, further comprising sensors configured to determine whether the x-ray camera is aligned with the x-ray source, the sensors selected from at least one of transmitters, receivers, and transceivers, the transmitters selected from at least one of an LED, an x-ray beam, and a laser and the receivers selected from at least one of a photodiode and a laser diode.

* * * * *